US 6,654,636 B1

(12) United States Patent
Dev et al.

(10) Patent No.: US 6,654,636 B1
(45) Date of Patent: Nov. 25, 2003

(54) SKIN AND MUSCLE-TARGETED GENE THERAPY BY PULSED ELECTRICAL FIELD

(75) Inventors: Nagendu B. Dev, San Diego, CA (US); Gunter A. Hofmann, San Diego, CA (US); Edward Nolan, San Diego, CA (US); Dietmar P. Rabussay, San Diego, CA (US); Arnt Tonnessen, El Cajon, CA (US); Georg Widera, Del Mar, CA (US); Lei Zhang, San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 204 days.

(21) Appl. No.: 09/625,825

(22) Filed: Jul. 26, 2000

Related U.S. Application Data

(62) Division of application No. 09/352,809, filed on Jul. 13, 1999.
(60) Provisional application No. 60/126,058, filed on Mar. 25, 1999, provisional application No. 60/109,324, filed on Nov. 20, 1998, and provisional application No. 60/092,544, filed on Jul. 13, 1998.

(51) Int. Cl.[7] .......................... A61N 1/30; A61M 31/00
(52) U.S. Cl. ........................................ 604/21; 604/501
(58) Field of Search ........................ 604/20–21, 49, 604/313–316, 501; 606/41, 42, 44, 48–50; 607/115, 120

(56) References Cited

U.S. PATENT DOCUMENTS

| 1,653,819 | A |   | 12/1927 | Northcott et al. |          |
|-----------|---|---|---------|------------------|----------|
| 4,262,672 | A |   | 4/1981  | Kief             |          |
| 4,907,601 | A |   | 3/1990  | Frick            |          |
| 4,991,578 | A | * | 2/1991  | Cohen            | 128/419  |
| 5,019,034 | A |   | 5/1991  | Weaver et al.    |          |
| 5,053,001 | A | * | 10/1991 | Reller et al.    | 604/20   |
| 5,058,605 | A |   | 10/1991 | Slovak           |          |
| 5,215,088 | A |   | 6/1993  | Normann et al.   |          |
| 5,273,525 | A |   | 12/1993 | Hofmann          |          |
| 5,279,544 | A | * | 1/1994  | Gross et al.     | 604/20   |
| 5,284,471 | A | * | 2/1994  | Sage, Jr.        | 604/20   |
| 5,304,120 | A |   | 4/1994  | Crandell et al.  |          |
| 5,306,236 | A | * | 4/1994  | Blumenfeld et al.| 604/21   |
| 5,309,909 | A | * | 5/1994  | Gadsby et al.    | 128/639  |
| 5,322,520 | A | * | 6/1994  | Milder           | 604/265  |
| 5,328,451 | A |   | 7/1994  | Davis et al.     |          |
| 5,389,069 | A |   | 2/1995  | Weaver           |          |
| 5,425,752 | A |   | 6/1995  | Vu'Nguyen        |          |
| 5,439,440 | A |   | 8/1995  | Hofmann          |          |
| 5,468,223 | A |   | 11/1995 | Mir              |          |
| 5,507,724 | A |   | 4/1996  | Hofmann et al.   |          |

(List continued on next page.)

FOREIGN PATENT DOCUMENTS

| DE | 863 111      | 1/1953  |
| DE | 40 00 893 A1 | 1/1990  |
| EP | 0 378 132 A2 | 1/1990  |
| EP | 0 378 132 A3 | 1/1990  |
| WO | WO97/07826   | 3/1997  |
| WO | WO99/44678   | 9/1999  |
| WO | WO99/52424   | 10/1999 |

OTHER PUBLICATIONS

Zhang, et al., "Depth Targeted Efficient Gene Deliver and Expression in the Skin by Pulsed Electric Fields: An Approach to Gene Therapy of Skin Aging and Other Diseases," *Biochemical Biophysical. Research Communications* 220 (3):633–636 (1996).

*Primary Examiner*—Sharon Kennedy
(74) *Attorney, Agent, or Firm*—Gray Cary Ware & Freidenrich, LLP; Lisa A. Haile; June M. Learn

(57) ABSTRACT

The present invention describes an in vivo method, using pulsed electric field to deliver therapeutic agents into cells of the skin and muscle for local and systemic treatments. In particular, therapeutic agents include naked or formulated nucleic acid, polypeptides and chemotherapeutic agents.

7 Claims, 19 Drawing Sheets

U.S. PATENT DOCUMENTS

| | | | |
|---|---|---|---|
| 5,507,802 A | 4/1996 | Imran | |
| 5,536,267 A | 7/1996 | Edwards et al. | |
| 5,547,467 A | 8/1996 | Pliquett et al. | |
| 5,554,110 A | 9/1996 | Edwards et al. | |
| 5,667,491 A | 9/1997 | Pliquett et al. | |
| 5,674,267 A | 10/1997 | Mir et al. | |
| 5,702,359 A | 12/1997 | Hofmann et al. | |
| 5,718,702 A | 2/1998 | Edwards | |
| 5,720,921 A | 2/1998 | Meserol | |
| 5,749,847 A | 5/1998 | Zewert et al. | |
| 5,780,052 A | 7/1998 | Khaw et al. | |
| 5,786,454 A | 7/1998 | Waksman et al. | |
| 5,789,213 A | 8/1998 | Hui et al. | |
| 5,807,308 A | 9/1998 | Edwards | |
| 5,807,309 A | 9/1998 | Lundquist et al. | |
| 5,810,762 A | 9/1998 | Hofmann | |
| 5,814,599 A | 9/1998 | Mitragotri et al. | |
| 5,845,646 A | 12/1998 | Lemelson | |
| 5,868,740 A | 2/1999 | LeVeen et al. | |
| 5,869,326 A | 2/1999 | Hofmann | |
| 5,873,849 A | 2/1999 | Bernard | |
| 5,874,268 A | 2/1999 | Meyer | |
| 5,879,891 A | 3/1999 | Thompson | |
| 5,908,753 A | 6/1999 | Kelly et al. | |
| 5,911,223 A | 6/1999 | Weaver et al. | |
| 5,944,715 A | 8/1999 | Goble et al. | |
| 5,964,726 A * | 10/1999 | Korenstein et al. | 604/20 |
| 5,968,006 A | 10/1999 | Hofmann | |
| 5,972,013 A * | 10/1999 | Schmidt | 606/185 |
| 5,980,517 A | 11/1999 | Gough | |
| 5,983,131 A | 11/1999 | Weaver et al. | |
| 5,983,136 A * | 11/1999 | Kamen | 604/21 |
| 5,993,434 A | 11/1999 | Dev et al. | |
| 5,994,127 A | 11/1999 | Selden et al. | |
| 5,995,869 A | 11/1999 | Cormier et al. | |
| 6,001,617 A | 12/1999 | Raptis | |
| 6,002,961 A | 12/1999 | Mitragotri et al. | |
| 6,110,161 A | 8/2000 | Mathiesen et al. | |
| 6,206,004 B1 * | 3/2001 | Schmidt et al. | 128/898 |
| 6,277,116 B1 * | 8/2001 | Utely et al. | 606/42 |
| 6,330,478 B1 * | 12/2001 | Lee et al. | 607/101 |

* cited by examiner

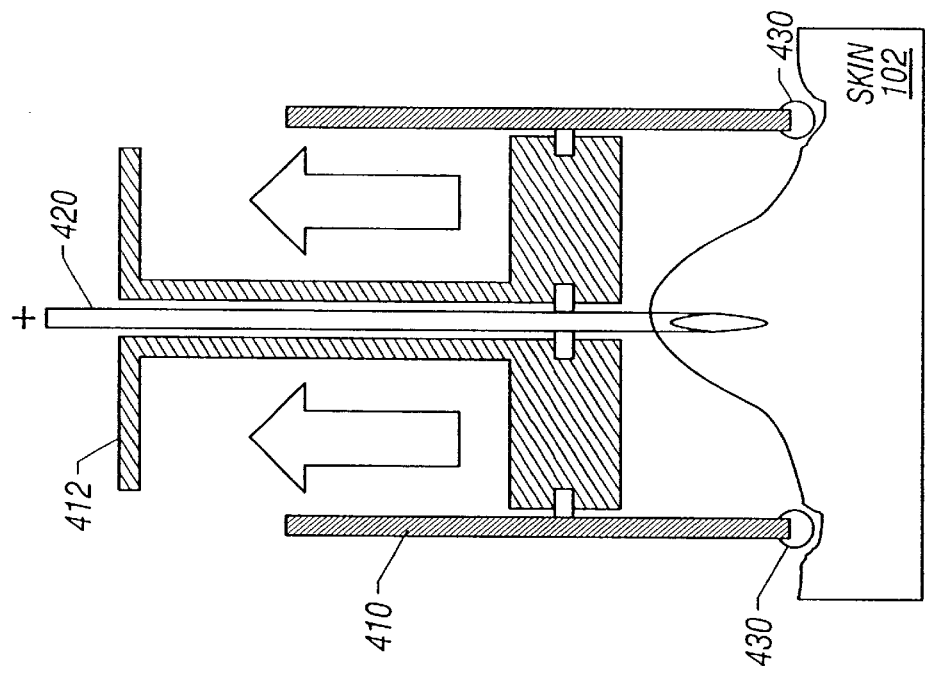
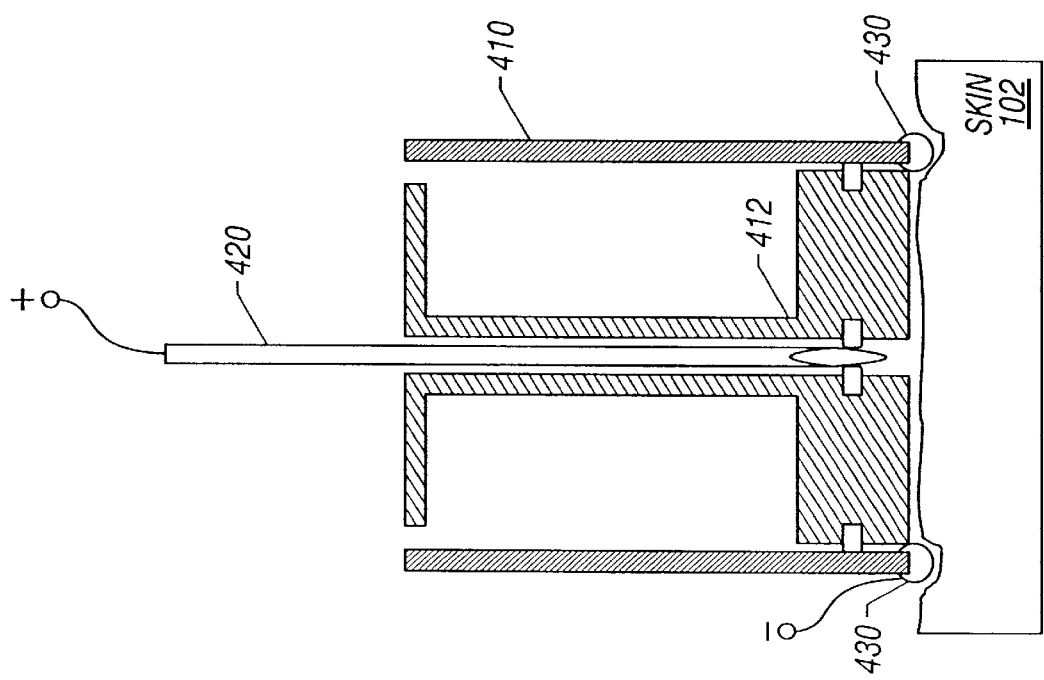

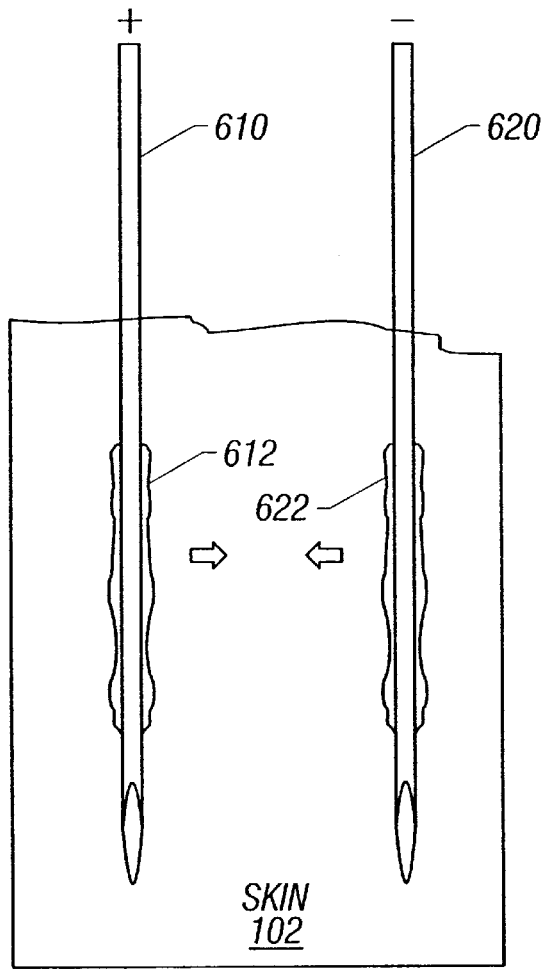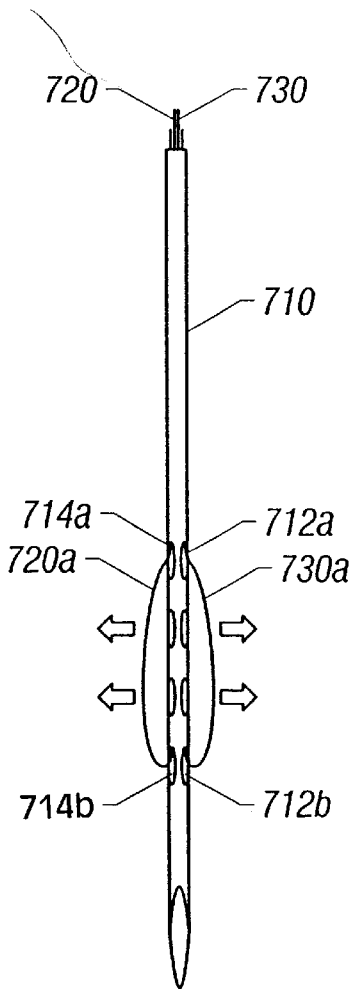
FIG. 6
FIG. 7

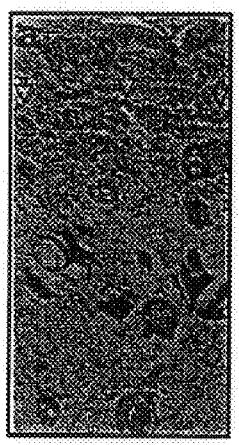 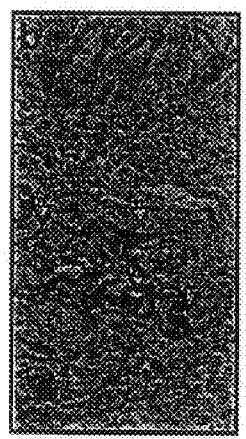 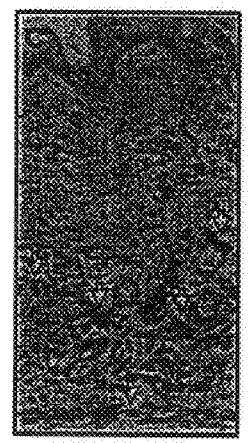 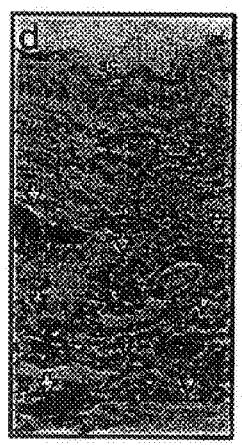
| Pressure only | EP (10 ms) + 1 min | EP (10 ms) + 10 min | EP (20 ms) + 10 min |
| --- | --- | --- | --- |
| FIG. 13A | FIG. 13B | FIG. 13C | FIG. 13D |

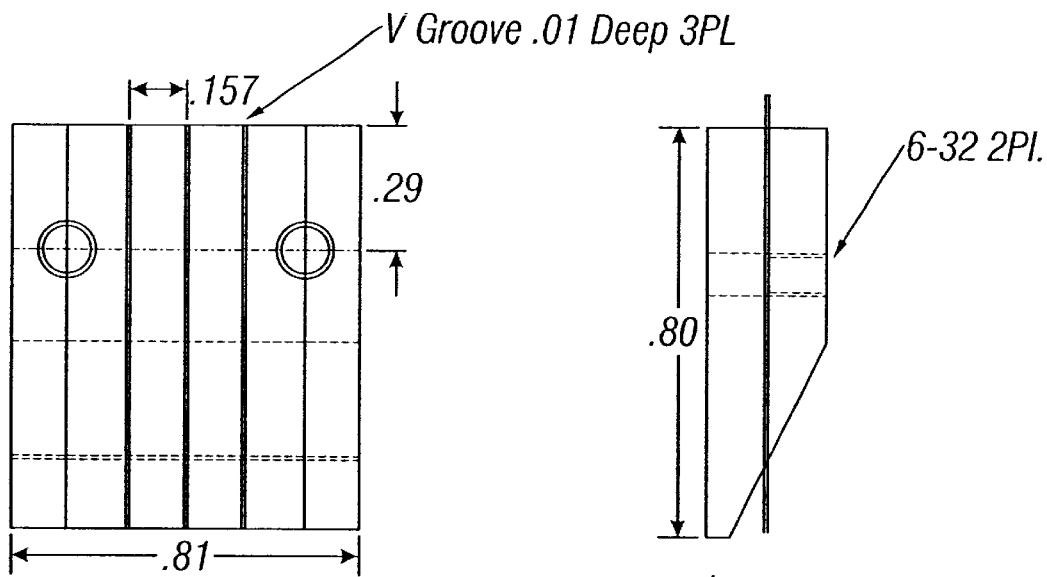
FIG. 20A
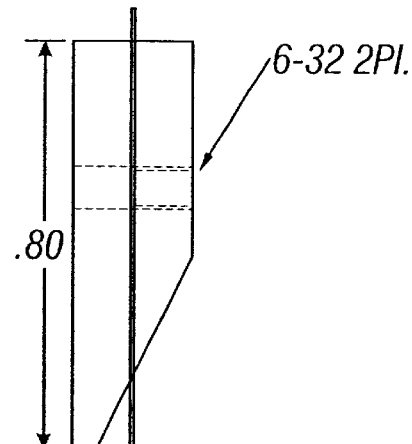
FIG. 20B
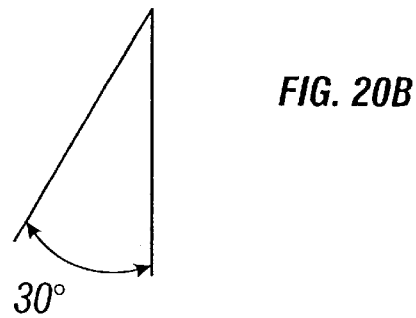
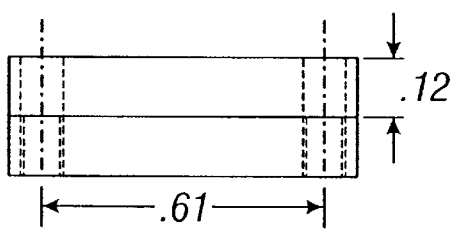
FIG. 20C
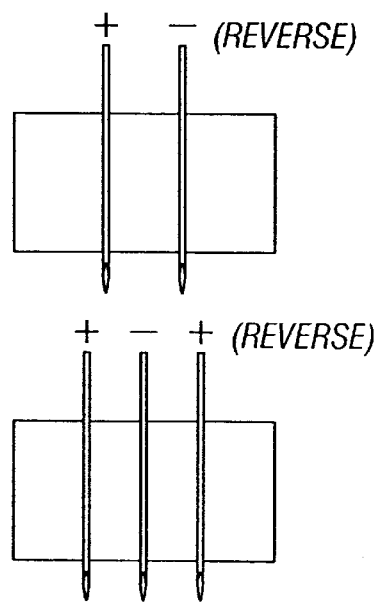
FIG. 20D

SKIN AND MUSCLE-TARGETED GENE THERAPY BY PULSED ELECTRICAL FIELD

RELATED APPLICATIONS

This application is a divisional application of U.S. patent application Ser. No. 09/352,809 filed Jul. 13, 1999, now pending; which claims priority under 35 USC §119(e) to U.S. patent application Ser. No. 60/126,058 filed Mar. 25, 1999, now abandoned; U.S. patent application Ser. No. 60/109,324 filed Nov. 20, 1998, now abandoned; and U.S. patent application Ser. No. 60/092,544 filed Jul. 13, 1998, now abandoned, the entire contents of each is incorporated herein by reference.

FIELD OF THE INVENTION

The present invention relates generally to the use of electric pulses to increase the permeability of cells, and more specifically to a method and apparatus for the application of controlled electric fields for in vivo delivery of pharmaceutical compounds and genes into cells by electroporation therapy (EPT), also known as cell poration therapy (CPT) and electrochemotherapy (ECT).

BACKGROUND OF THE INVENTION

The skin is an especially attractive target for gene therapy. In particular, the ability to target genes to the epidermis of the skin could be used to correct skin-specific disorders as well as for the production of proteins secreted into the skin to correct certain systemic diseases. For example, genes expressing cytokines, interferons or other biologically active molecules could be used to treat skin tumors or other lesions. In addition, keratinocytes and fibroblasts in the skin can secrete protein factors which circulate to treat systemic conditions such as hemophilia. Despite the clear potential in using skin as a target for gene therapy, the major technical problem of an in vivo method of gene delivery remains largely unresolved. Since the stratum corneum (SC) acts as a significant physical barrier to gene transfer into the skin, the technical problem of how to deliver genes through this layer persists.

Similarly, muscle cells are also useful targets for gene therapy due to their ubiquity. Nonetheless, as with skin, there exists a need for a method to reliably introduce exogenous therapeutic material into muscle cells.

Gene therapy does not include only intrinsically therapeutic genetic material (i.e., genes that encode a missing or underexpressed gene product), but also those which elicit an immune response. One of the oldest and most effective forms of preventative care against infectious diseases is vaccination. Safe and effective vaccines are available to protect against a variety of bacterial and viral diseases. These vaccines consist of inactivated pathogens, recombinant of natural subunits, and live attenuated or live recombinant microorganisms.

DNA immunization, a novel method to induce protective immune responses, was recently introduced into the scientific community and proven to be very effective in animal models. This technology is currently in first safety and efficacy trials in human volunteers. DNA immunization entails the direct, in vivo administration of plasmid-based DNA vectors that encode the production of defined microbial antigens. The de novo production of these antigens in the host's own cells results in the elicitation of antibody (i.e., humoral) and cellular immune responses that provide protection against live virus challenge and persist for extended periods in the absence of further immunizations. The unique advantage of this technology is its ability to mimic the effects of live attenuated vaccines without the safety and stability concerns associated with the parenteral administration of live infectious agents. Because of these advantages, considerable research efforts have focused on refining in vivo delivery systems for naked DNA that result in maximal antigen production and resultant immune responses.

The most widely used administration of vaccine DNA is direct injection of the DNA into muscle or skin by needle and syringe. This method is effective in inducing immune responses in small animals, as mice, but even here it requires the administration of relatively large amounts of DNA, ca. 50 to 100 ug per mouse. To obtain immune responses in larger animals, as rabbits, non-human primates, and humans, very large amounts of DNA have to be injected. It has to be seen whether this requirement for very large amounts of vaccine DNA turns out to be practical, for safety and commercial reasons, in human applications.

A cell has a natural resistance to the passage of molecules through its membranes into the cell cytoplasm. Scientists in the 1970's first discovered "electroporation", where electrical fields are used to create pores in cells without causing permanent damage to the cells. Electroporation made possible the insertion of large molecules directly into cell cytoplasm by temporarily creating pores in the cells through which the molecules pass into the cell.

Electroporation techniques (both in vitro and in vivo) function by applying a brief high voltage pulse to electrodes positioned around the treatment region. The electric field generated between the electrodes causes the cell membranes to temporarily become porous, whereupon molecules of the implant agent enter the cells.

Electroporation has been used to implant materials into many different types of cells. Such cells, for example, include eggs, platelets, human cells, red blood cells, mammalian cells, plant protoplasts, plant pollen, liposomes, bacteria, fungi, yeast, and sperm. Furthermore, electroporation has been used to implant a variety of different materials, including nucleic acids, polypeptides, and various chemical agents.

Electroporation has been used in both in vitro and in vivo procedures to introduce foreign material into living cells. With in vitro applications, a sample of live cells is first mixed with the implant agent and placed between electrodes such as parallel plates. Then, the electrodes apply an electrical field to the cell/implant mixture.

With in vivo applications of electroporation, electrodes are provided in various configurations such as, for example, a caliper that grips the epidermis overlying a region of cells to be treated. Alternatively, needle-shaped electrodes may be inserted into the patient, to access more deeply located cells. In either case, after the therapeutic agent is injected into the treatment region, the electrodes apply an electrical field to the region. In some electroporation applications, this electric field comprises a single square wave pulse on the order of 100 to 500 V/cm, of about 10 to 60 ms duration. Such a pulse may be generated, for example, in known applications of the Electro Square Porator T820, made by the BTX Division of Genetronics, Inc.

Electroporation has been recently suggested as an alternate approach to the treatment of certain diseases such as cancer by introducing a chemotherapy drug directly into the cell. For example, in the treatment of certain types of cancer with chemotherapy it is necessary to use a high enough dose of a drug to kill the cancer cells without killing an unacceptable high number of normal cells. If the chemotherapy drug could be inserted directly inside the cancer cells, this objective could be achieved. Some of the best anti-cancer drugs, for example, bleomycin, normally cannot penetrate the membranes of certain-cancer cells effectively. However, electroporation makes it possible to insert the bleomycin into the cells.

Despite the suitability of the epidermis as a target tissue for gene therapy, there are significant barriers to safe, easy, efficient, and economical gene delivery. In particular, the lipid-rich SC, which is composed of dead keratinocytes surrounded by multiple, parallel bilayer membranes, represents a formidable physical barrier to epidermal gene transfer. To overcome this barrier a novel, non-viral approach, involving the basic concept of electroporation to introduce genes into the epidermis is provided by the present invention.

As described above, the technique of electroporation is now a well-established physical method for transfection of cells that allows introduction of marker molecules, drugs, genes, antisense oligonucleotides and proteins intracellularly. However, there still exists a need to introduce therapeutic agents directly into skin cells or through the skin and into muscle cells without direct injection.

BRIEF DESCRIPTION OF THE INVENTION

The present invention describes an in vivo method, using pulsed electric field to deliver therapeutic agents into cells of the skin and muscle for local and systemic treatments. In particular, therapeutic agents include naked or formulated nucleic acid, polypeptides and chemotherapeutic agents.

Therapeutic agents can be employed directly as palliative agents (i.e., those which directly exert a therapeutic effect), or as agents with a less direct effect (e.g., genes encoding polypeptides that elicit an immune response).

The advantages offered by electroporation for skin and muscle-directed gene therapy include: (1) elimination of the risk of generating novel disease-causing agents, (2) delivery of DNA molecules much larger than can be packaged into a virus, (3) no immune responses or toxic side effects by non-DNA material, e.g., viral proteins or cationic lipids, (4) DNA enters the cell through a non-endosomal pathway, diminishing the rate of DNA degradation, and (5) the method is simple, highly reproducible and cost-effective.

In accordance with one embodiment of the present invention, there is provided an in vivo method for introducing a therapeutic agent into skin cells of a subject, comprising applying a pulsed electric field to the skin cells substantially contemporaneously with the application of therapeutic agent to the skin cells, such that the therapeutic agent is introduced into the skin cells.

In accordance with another embodiment of the present invention, there is provided a method for inducing an immune response in a subject, comprising applying a pulsed electric field to skin and/or muscle cells of the subject substantially contemporaneously with the application of an immune response-inducing agent to the skin and/or muscle cells, such that the immune response-inducing agent is introduced into the skin and/or muscle cells thereby inducing in the subject an immune response.

In accordance with still another embodiment of the present invention, there is provided a method for the therapeutic application of electroporation to skin and/or muscle cells of a subject for introducing topically applied molecules into said cells, comprising providing an array of electrodes, at least one of the electrodes having a needle configuration for penetrating tissue; inserting the needle electrode into selected tissue; positioning a second electrode of the array of electrodes in conductive relation to the selected tissue; and applying pulses of high amplitude electric signals to the electrodes, proportionate to the distance between the electrodes, for electroporation of said tissue; such that said topically applied molecules are introduced into said skin and/or muscle cells.

In another embodiment of the present invention, there is provided a micropatch electrode for use with an electroporation apparatus, said micropatch electrode having a substantially planar array of patch elements, each patch element comprising two sets of electrodes, wherein each set of electrodes comprises a first electrode and a second electrode electrically insulated from one another, such that when different electric potentials are applied to said first and second electrodes, a voltage is produced therebetween.

An electrode kit for use in conjunction with electroporation therapy, said kit having a micropatch electrode as described herein, and an injection needle, optionally comprising one or more holes disposed along its length and proximal to the needle tip, wherein said holes are in fluid communication with the hollow interior of said injection needle.

In accordance with another embodiment of the present invention there is provided an electrode for use with an electroporation apparatus, said electrode having a ring-shaped electrode having an electrically insulating shield, wherein the electrically insulating shield provides support to the ring-shaped electrode and electrically insulates a tissue under treatment employing the electrode, and an electrically conducting injection needle, optionally comprising one or more holes disposed along its length and proximal to the needle tip, wherein the holes are in fluid communication with the hollow interior of the injection needle, wherein a potential difference applied to the ring-shaped electrode and the needle electrode creates a voltage therebetween.

In accordance with yet another embodiment of the present invention there is provided an electrode for use with an electroporation apparatus, said electrode having an array of a plurality of paired electrode needles and, at least one injection needle, wherein a potential difference applied said paired electrode needles creates a voltage therebetween.

In accordance with another embodiment of the present invention there is provided an electrode for use with an electroporation apparatus, said electrode having a suction generating device comprising a ring electrode disposed about an injection needle electrode, such that when said ring electrode is contacted with skin of a subject and suction is generated by the suction generating device, the skin is pulled up around the injection needle electrode, causing the injection needle electrode to pierce the skin, and wherein a potential difference applied to the ring-shaped electrode and said injection needle electrode creates a voltage therebetween.

In accordance with another embodiment of the present invention there is provided an electrode for use with an electroporation apparatus, said electrode having an injection needle and paired electrically conducting wires disposed within the hollow core of the injection needle and protruding from the tip thereof, the electrically conducting wires having an electrically insulated portion and an exposed electrically conducting portion, the exposed electrically conducting portion being at the end of said wires protruding from the tip of said injection needle.

In accordance with another embodiment of the present invention there is provided a needle electrode for use with an electroporation apparatus, said needle electrode having disposed around a portion of its length a substance-releasing material.

In accordance with another embodiment of the present invention there is provided a needle electrode for use with an electroporation apparatus, said needle electrode having a hollow central core, at least four holes along its length, wherein the four holes comprise two paired holes, each of said two paired holes comprising a hole proximal to the tip of the needle and a hole distal to the tip of said needle, and a pair of electrically conducting wires having an electrically insulated portion and an exposed electrically conducting portion, wherein the pair of electrically conducting wires are located in said hollow core, except for the exposed electrically conducting portion which runs outside of the needle, extending outward from the distal paired hole to the proximal paired hole where it re-enters the hollow core.

In accordance with another embodiment of the present invention there is provided a needle electrode for use with an electroporation apparatus, said electrode having a plurality of electrically conducting needles disposed within a depth guide, wherein the tip of the needles extend for a predetermined distance beyond the depth guide.

BRIEF DESCRIPTION OF THE FIGURES

FIGS. 4A and 4B show an electroporation device according to an embodiment of the invention. A syringe 410 is implemented to hold an injection needle electrode 420 and a ring electrode 430.

FIG. 6 shows a pair of needle electrodes 610 and 620 that have substance-releasing sections 612 and 622 near the needle tips.

FIG. 7 shows a single needle applicator having a hollow center portion and at least four holes 712A, 712B, 714A, and 714B on the side walls near the needle tip.

FIG. 13, panels a–d, depict photomicrographs of skin samples stained with X-gal, and: (a) no pulse (caliper pressure only); (b) three pulses and caliper pressure treatment for 1 min.; (c) and (d) after the same treatment as panel (b) but with increased pulse length and post-pulse pressure time. pulse pressure times of 10 ms with 10 min. pressure and 20 ms with 10 min. pressure, respectively.

FIG. 16A shows GFP expressing cells are visible (100× magnification, fluorescent light only). FIG. 16B shows the GFP positive and negative cells (460× magnification) illuminated with white and fluorescent lights.

FIGS. 20A–20D depict an alternative embodiment of a shallow needle electrode array.

DETAILED DESCRIPTION OF THE INVENTION

Figure 1:
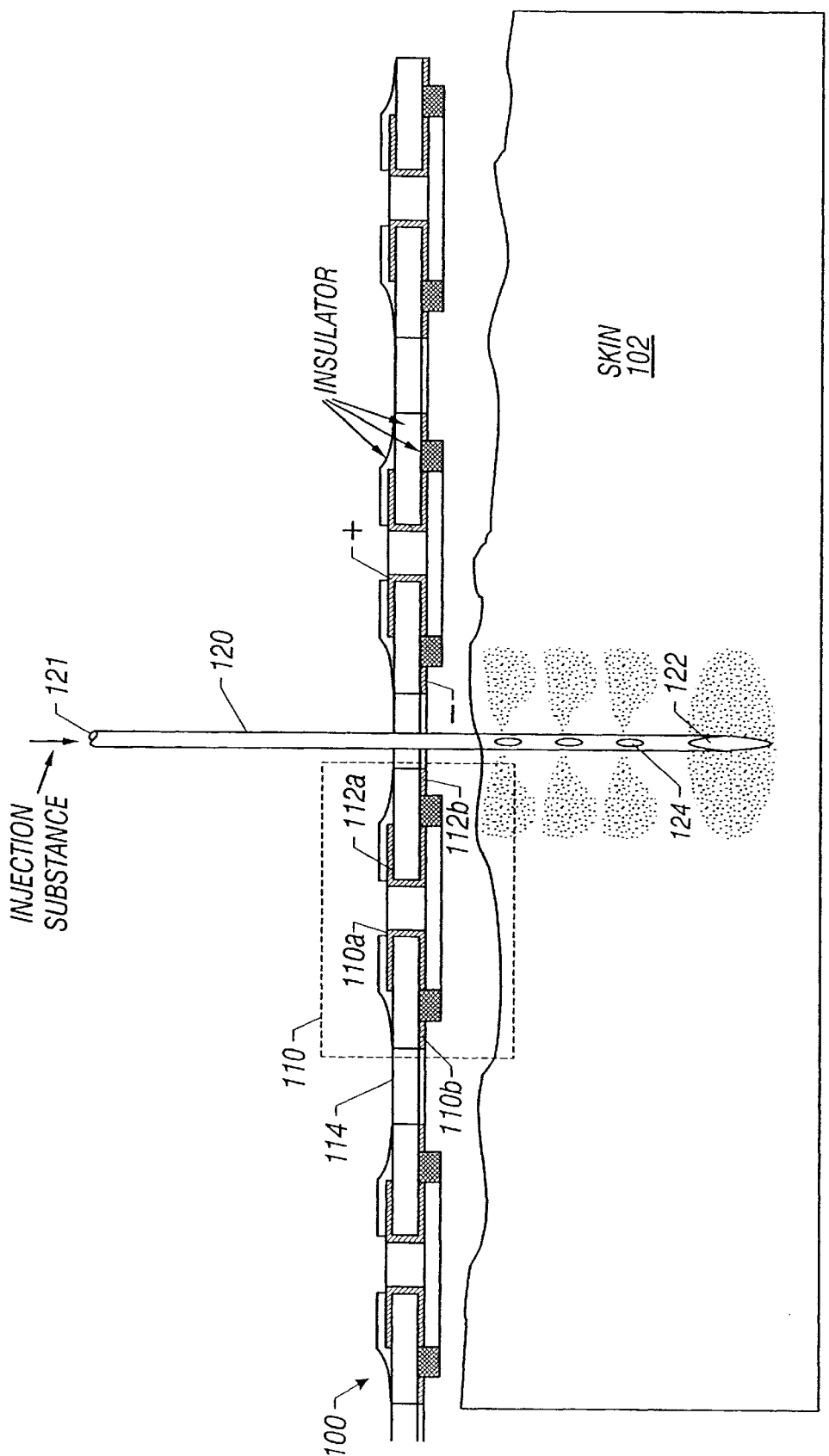
FIG. 1 shows a micropatch electroporation applicator that has a micropatch member 110 and an injection needle 120.

In accordance with the present invention, there are provided in vivo methods for introducing a therapeutic agent into skin or muscle cells of a subject, said method comprising applying a pulsed electric field to said skin or muscle cells substantially contemporaneously with the application of said therapeutic agent to said skin or muscle cells, such that said therapeutic agent is introduced into said skin or muscle cells respectively.

The term "substantially contemporaneously" means that the molecule and the electroporation treatment are administered reasonably close together with respect to time. The administration of the molecule or therapeutic agent can at any interval, depending upon such factors, for example, as the nature of the tumor, the condition of the patient, the size and chemical characteristics of the molecule and half-life of the molecule.

As used herein, the terms "impulse," "pulse," "electrical impulse," "electrical pulse," "electric pulse," "electropulse" and grammatical variations thereof are interchangeable and all refer to an electrical stimulus. Although the various terms are frequently used herein in the singular, the singular forms of the terms include multiple pulses. Preferred electrical impulses are pulsed electric fields applied via electroporation. The pulse can be unipolar, bipolar, exponential or square wave form. Electric pulses contemplated for use in the practice of the present invention include those pulses of sufficient voltage and duration to cause electroporation.

As used herein, the term "therapeutic agent" as used herein refers to drugs (e.g., chemotherapeutic agents), nucleic acids (e.g., polynucleotides), peptides and polypeptides, including antibodies. The term "polynucleotides" include DNA, cDNA and RNA sequences, as further elaborated herein.

Therefore, in accordance with another embodiment, the present invention provides a method for the introduction of nucleic acid into the cells of the skin and/or muscle, preferably human, by contacting the skin with nucleic acid and applying an electrical pulse to the targeted region. The electrical pulse is of sufficient voltage and duration to cause electroporation to happen so that the nucleic acid can penetrate into the cells of the skin and/or muscle and be expressed as a transgenic molecule. The biological expression of the nucleic acid component results in the transcription and translation of the delivered gene so that the targeted cells synthesize gene product de novo. Therapeutic applications include, for example, the augmentation of missing or under-expressed genes; the expression of genes that have a therapeutic value (e.g., inhibiting the action of harmful gene products by expressing a receptor to bind the product of an over-expressed gene); the expression of genes, the product of which elicits a desired immune response; and the like.

As will be understood by those of skill in the art, efficient expression of a nucleic acid encoding a therapeutic polypeptide generally requires that the nucleic acid sequence be operably associated with a regulatory sequence. Regulatory sequences contemplated for use in the practice of the present invention include promoters, enhancers, and the like. As those of skill in the art will also appreciate, even when a promoter sequence is operably associated with the therapeutic nucleic acid, expression may be further augmented by operably associating an enhancer element or the like.

Promoters contemplated for use in the practice of the present invention include the CMV, RSV LTR, MPSV LTR, SV40, the group of keratin specific promoters (e.g., the keratin and involucrin group of promoters. Presently, it is preferred that the promoters employed in the practice of the present invention are specifically active in skin cells. The transcriptional promoters of a number of genes expressed in the epidermis have been characterized. Furthermore, such promoters tend to restrict expression to either the basal compartment or the suprabasal compartment. Keratin 14, for example, is expressed by basal keratinocytes, whereas involucrin is expressed by suprabasal keratinocytes. In addition, the keratin 14 and involucrin genes are highly expressed in keratinocytes, thus use of their promoters to drive transgene transcription yields not only target specificity, but also high levels of expression. The promoters for both genes have been successfully used to direct compartment-specific expression to the epidermis of transgenic mice.

Chemotherapeutic agents contemplated for use in the method of the invention typically have an antitumor or cytotoxic effect. Such drugs or agents include bleomycin, neocarcinostatin, suramin, doxorubicin, carboplatin, taxol, mitomycin C, cisplatin, and the like. Other chemotherapeutic agents will be known to those of skill in the art (see, for example The Merck Index). In addition, chemotherapeutic agents that are "membrane-acting" agents are also included in invention methods. These agents may have palliative effects as those listed above, or alternatively, they may be agents which act primarily by damaging the cell membrane. Examples of membrane-acting agents include N-alkylmelamide and para-chloro mercury benzoate. The chemical composition of the agent will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Further, such drugs as bleomycin, which have a very negative log P, (P being the partition coefficient between octanol and water), are very large in size (MW=1400), and are hydrophilic, thereby associating closely with the lipid membrane, diffuse very slowly into a tumor cell and are typically administered prior to or substantially simultaneous with the electric pulse. In addition, certain agents may require modification in order to allow more efficient entry into the cell. For example, an agent such as taxol can be modified to increase solubility in water which would allow more efficient entry into the cell. Electroporation facilitates entry of bleomycin or other similar drugs into the tumor cell by creating pores in the cell membrane.

In one embodiment of the present invention, there is provided a method for the therapeutic application of electroporation to skin and/or muscle of a subject for introducing applied molecules into cells therein, comprising providing an array of electrodes, at least one of the electrodes having a needle configuration for penetrating tissue; inserting the needle electrode into selected tissue; positioning a second electrode of the array of electrodes in conductive relation to the selected tissue; applying pulses of high amplitude electric signals to the electrodes, proportionate to the distance between the electrodes, for electroporation of the tissue, such that said applied molecules are introduced into said skin or muscle cells. In one aspect of the present invention, the molecules to be introduced are topically applied. In another aspect of the present invention, the molecules to be introduced are applied by other means such as injection, or the like. It should be understood that the electroporation of tissue can be performed in vitro, in vivo, or ex vivo. Electroporation can also be performed utilizing single cells, e.g., single cell suspensions or in vitro or ex vivo in cell culture.

It may be desirable to modulate the expression of a gene in a cell by the introduction of a molecule by the method of the invention. The term "modulate" envisions the suppression of expression of a gene when it is over-expressed, or augmentation of expression when it is under-expressed. Where a cell proliferative disorder is associated with the expression of a gene, for example, nucleic acid sequences that interfere with expression of the gene at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Nucleic acids contemplated for use in the practice of the present invention include naked DNA, naked RNA, naked plasmid DNA, either supercoiled or linear, and encapsulated DNA or RNA (e.g., in liposomes, microspheres, or the like). As will be understood by those of skill in the art, particles mixed with plasmid so as to "condense" the DNA molecule may also be employed.

Antisense nucleic acids are DNA or RNA molecules that are complementary to at least a portion of a specific mRNA molecule (see, e.g., Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause deleterious effects than larger molecules when introduced into the target cell. The use of antisense methods to inhibit the in vitro translation of genes is well known in the art (see, e.g., Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991). Accordingly, electroporation of nucleic acids useful for triplex formation is also contemplated as within the scope of the present invention.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while hammerhead-type ribozymes recognize base sequences in the range of 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides methods of gene therapy for the treatment of cell proliferative or immunologic disorders mediated by a particular gene or absence thereof. The term "cell proliferative disorder" denotes malignant as well as non-malignant cell populations which often appear to differ from the surrounding tissue both morphologically and genotypically. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as "naked" DNA for example.

The polynucleotide sequences of the invention are DNA or RNA sequences having a therapeutic effect after being taken up by a cell. Nucleic acids contemplated for use in the practice of the present invention can be double stranded DNA (e.g., plasmid, cosmid, phage, viral, YACS, BACS, other artficial chromsomes, and the like), single stranded DNA or RNA. The nucleic acids may be uncomplexed (i.e., "naked") or complexed (e.g., with chemical agents such as lipids (e.g., cationic), dendrimers, or other polyplexes that facilitate DNA penetration into tissues and through cell membranes, and the like). The DNA may also be encapsulated or formulated with protein complexes.

Examples of polynucleotides that are themselves therapeutic are anti-sense DNA and RNA; DNA coding for an anti-sense RNA; or DNA coding for tRNA or rRNA to replace defective or deficient endogenous molecules, and the like. The polynucleotides of the invention can also code for therapeutic polypeptides. As used herein, "polypeptide" is understood to be any translation product of a polynucleotide regardless of size, and whether glycosylated or not. Therapeutic polypeptides contemplated for use in the practice of the present invention include, as a primary example, those polypeptides that can compensate for defective or deficient species in an animal, or those that act through toxic effects to limit or remove harmful cells from the body.

Also included are polynucleotides which encode metabolic enzymes and proteins, such as blood coagulation compounds (e.g., Factor VIII or Factor IX), and the like.

In accordance with another embodiment of the present invention, there are provided methods for inducing an immune response in a subject. Invention methods of this embodiment comprise applying a pulsed electric field to skin or muscle cells of the subject substantially contemporaneously with the application of an immune response-inducing agent to the skin or muscle cells, such that the immune response-inducing agent is introduced into the skin or muscle cells thereby inducing in the subject an immune response. As used herein, "immune response-inducing agent" means any agent, which upon introduction into the skin or muscle cells of a subject, results in an immune response, whether the response be a cellular response, a humoral response, or both. Immune response-inducing agents contemplated for use in the practice of the present invention include expressible nucleic acids, and polypeptides.

Expressible DNA and mRNA can be delivered to cells to form therein a polypeptide translation product. If the nucleic acids are operatively associated with the proper regulatory sequences, enhanced synthesis of the encoded protein is achievable. DNA or RNA encoded polypeptides contemplated for use in the practice of the present invention include immunizing polypeptides, pathogen-derived proteins, blood coagulation factors, peptide hormones, and the like. Peptide hormones include, for example, calcitonin (CT), parathyroid hormone (PTH), erythropoietin (Epo), insulin, cytokines, growth hormone, growth factors, and the like). Lymphokines contemplated for use in the practice of the present invention include tumor necrosis factor, interleukins 1, 2, and 3, lymphotoxin, macrophage activating factor, migration inhibition factor, colony stimulating factor, alpha-interferon, beta-interferon, gamma-interferon and subtypes thereof. Blood coagulation factors contemplated for use in the practice of the present invention include Factor VIII or Factor IX.

When the DNA or mRNA delivered to the cells codes for an immunizing peptide, invention methods can be applied to achieve improved and more effective immunity against infectious agents, including bacteria, intracellular viruses, tumor cells, and the like. Therapeutic polynucleotides provided by the invention can also code for immunity-conferring polypeptides, which can act as endogenous immunogens (i.e., antigen-containing polypeptides) to provoke a humoral immune response, a cellular immune response-inducing agent response, or both. Methods for inducing such responses and targeting specific cells for specific responses are described, for example, in U.S. Pat. No. 5,589,466. The polynucleotides employed in accordance with the present invention can also code for an antibody. In this regard, the term "antibody" encompasses whole immunoglobulin of any class, chimeric antibodies and hybrid antibodies with dual or multiple antigen or epitope specificities, and fragments, such as $F(ab)_2$, Fab', Fab, and the like, including hybrid fragments thereof. Also included within the meaning of "antibody" are conjugates of such fragments, and so-called antigen binding proteins (single chain antibodies) as described, for example, in U.S. Pat. No. 4,704,692, hereby incorporated by reference herein in its entirety.

Thus, an isolated polynucleotide coding for variable regions of an antibody can be introduced, in accordance with the present invention, to enable the treated subject to produce antibody in situ. For illustrative methodology relating to obtaining antibody-encoding polynucleotides, see Ward et al. *Nature*, 341:544–546 (1989); Gillies et al., *Biotechnol.* 7:799–804 (1989). The antibody in turn exerts a therapeutic effect, for example, by binding a surface antigen associated with a pathogen. Alternatively, the encoded antibodies can be anti-idiotypic antibodies (antibodies that bind other antibodies) as described, for example, in U.S. Pat. No. 4,699,880. Such anti-idiotypic antibodies could bind endogenous or foreign antibodies in a treated individual, thereby ameliorating or preventing pathological conditions associated with an immune response, (e.g., in the context of an autoimmune disease such as lupus and the like).

It is presently preferred that polynucleotide sequences used in the practice of the present invention code for therapeutic or immunogenic polypeptides. These polynucleotide sequences may be used in association with other polynucleotide sequences coding for regulatory proteins that control the expression of the therapeutic or immunogenic polypeptides. The regulatory protein(s) so employed can act in any number of regulatory manners known to those of skill in the art, such as by binding to DNA so as to regulate its transcription, by binding to messenger RNA to increase or decrease its stability or translation efficiency, and the like.

The polynucleotide material delivered to the cells in vivo can take any number of forms, and the present invention is not limited to any particular polynucleotide coding for any particular polypeptide. Plasmids containing genes coding for a large number of physiologically active peptides and antigens or immunogens are contemplated for use in the practice of the present invention and can be readily obtained by those of skill in the art.

Various viral vectors can also be utilized in the practice of the present invention and include adenovirus, herpes virus, vaccinia, RNA virus, and the like. It is presently preferred that the virus be an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV), or the like can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. As used herein, the term "biological response modifiers" encompasses substances which are involved in modifying the immune response. Examples of immune response modifiers include such compounds as lymphokines, and the like. Lymphokines include, for example, tumor necrosis factor, interleukins 1, 2, and 3, lymphotoxin, macrophage activating factor, migration inhibition factor, colony stimulating factor, alpha-interferon, beta-interferon, gamma-interferon and their subtypes.

Administration of a chemotherapeutic agent, polynucleotide or polypeptide, in the practice of invention methods will typically be by topical application. Accordingly, a "permeation enhancer" also can be included with electropulsing to increase introduction of a composition. As used herein, the term "permeation enhancer" refers to any action (e.g., mechanical, physical, chemical) or any composition that can increase or "augment" introduction of a composition into skin and/or muscle cells. The term "augment," when used herein as a modifier of introduction, means that the rate (over time) or amount of composition introduced into skin and/or muscle cells via electropulsing is greater than that produced by electropulsing in the absence of the permeation enhancer. Thus, administering a permeation enhancer prior to, substantially contemporaneously with or after topical application of a therapeutic agent serves to "augment" electrically induced introduction of the composition into skin and/or muscle cells. Alternatively, a permeation enhancer can be mixed with the composition in the pharmaceutical formulation to be introduced. Permeation enhancer compositions that increase the permeability of skin and/or muscle cells include, for example, alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, methyl salicylate, and the like. Permeation enhancers further include mechanical or physical actions that function in association with an electrical impulse (e.g., abrasion, vibration, ultrasound, and the like).

Depending on the nature of the therapeutic agent, the desired depth of penetration, the target tissue type, and the like, it may be desirable to conduct electroporation in combination with other electrically-based treatment modalities. Electropulsing conducted substantially contemporaneously with iontophoresis (IPH), can produce a greater therapeutic effect than either applying the pulse or iontophoresis alone. Furthermore, electroincorporation (EI) (see, e.g., U.S. Pat. No. 5,464,386, which is hereby incorporated by reference herein in its entirety), or electropulsing in combination with IPH and liposomal formulation can enhance delivery significantly. (see, e.g., Badkar, et al., Drug Delivery 6 (1999) 111–115). Accordingly, in another embodiment of the present invention, electropulsing is used in conjunction with one or more of iontophoresis and electroincorporation.

As used herein, the term "transdermally introducing" and grammatical variations thereof, refers to the delivery of a composition into the skin, through/across the skin, or a combination thereof.

Targeting the cells of the skin for gene therapy has several advantages. First of all, the epidermis is an accessible tissue, which simplifies approaches for introduction of a transgene. Keratinocytes, the predominant cell type in the epidermis and hence the cellular target for gene transfer, form the outer-most barriers of the skin, making them amenable to in vivo manipulation. The accessibility of the epidermis raises the potential for use of non-invasive, topical methods for gene transfer. The epidermis is a stratified squamous epithelium consisting of a basal proliferating compartment and a suprabasal, differentiating compartment. By targeting gene transfer to the basal compartment, genes can be introduced into epidermal stem cells. Various treatment regimens are thus made possible. For example, single gene recessive disorders such as lamellar ichthyosis (LI) or X-linked ichthyosis (XLI) could be treated using the gene transglutaminase 1, or the gene for the steroid sulfatase arylsulfatase C, respectively. Epidermal stem cells give rise to basal, transiently amplifying cells, which have a limited capacity to divide. In turn, these cells give rise to the differentiating keratinocytes of the suprabasal epidermis. Thus, by achieving transgene expression in progenitor basal keratinocytes, methods for long-term, sustained gene therapy are provided.

Keratinocytes function well as synthetic and secretory cells. Keratinocytes have been shown to synthesize and secrete in-vivo the products of transfected genes. Circulating transgene-derived proteins such as growth hormone (GH) (22 kD), ApoE (34 kD), and FIX (57 kD) have been detected in athymic mice bearing grafts of keratinocytes. This demonstrates that transgene products expressed in the epidermis can penetrate the basement membrane zone and reach the systemic circulation.

1. In one embodiment, the electrode is a wire electrode (useful for in vitro studies, and the like). In another embodiment, the electrode is a plurality of electrodes (e.g., a micropatch electrode as described in U.S. patent application Ser. No. 09/134,245, filed on Aug. 14, 1998, which is hereby incorporated herein in its entirety by reference). In still yet another embodiment, the electrode comprises a meander electrode (e.g., an array of interweaving electrode fingers, with a typical electrode width in the range of about 0.2 up to about 1 mm, and an electrode gap of about 0.2 mm, wherein the gap can be filled with an electrically insulating substance). In an additional embodiment, the electrode is a porous electrode. The various electrodes used herein are preferably insulated to protect against excess heat or burning, current leakage, shock, etc. Appropriate electric pulsing parameters are set forth herein or can be determined using the teachings herein and, in view of these parameters, the skilled artisan can select among various suitable electrode types (e.g., ceramic, metal, etc.) and configurations (single wire, multiple wire, etc.) available in the art. In one embodiment of the present invention, a square wave pulse is applied, wherein the pulse is at least 50 V for about 10 up to 20 ms. Of course other pulse types, voltages and times may be appropriate, as will be understood by those of skill in the art.

In accordance with additional embodiments of the present invention, there are provided a number of improved electroporation devices that may be advantageously used in different applications. Examples of these additional embodiments are described below, with reference to attached figures.

FIG. 1 shows a micropatch electroporation applicator 100 that has a micropatch member 110 and an injection needle 120. The micropatch 100 includes a plurality of patch elements 110 that are positioned relative to one another to form a substantially planar array. Each patch element 110 includes two pairs of electrodes, a first pair having electrodes 110A and 110B and a second pair having electrodes 112A and 112B. The two electrodes 110A and 110B (or 112A and 112B) in each pair are electrically insulated from each other and are applied with different electrical potentials to produce a voltage therebetween. For example, the electrode 110A may be at a positive voltage and the electrode 110B may be at a negative voltage. An electrical control circuit (not shown) may be connected to the micropatch member 100 to produce desired electrical pulses at each patch element 110. One embodiment of the micropatch member 100 is disclosed in U.S. Pat. No. 6,055,433 entitled, "Method and Apparatus for Using Electroporation Mediated Delivery of Drugs and Genes," which is incorporated herein by reference in its entirety. The micropatch member 100 can be placed upon a tissue surface 102 such as a person's skin to apply electrical pulses to the tissue surface 102.

The micropatch member 100 also includes a plurality of gaps 114 between adjacent patch elements 110. Such gaps 114 are formed of an electrically insulating material and can be penetrated by sharp objects such as the injection needle 120. The injection needle 120 is configured to include a conduit 121 for transporting an injection substance to the needle tip 122. One or more holes 124 are optionally formed on the side walls of the needle 120 near the needle tip 122 so that the injection substance can be released not only from the needle tip 122 but also from these holes 124. The injection needle 120 may be formed of a metal but may also be formed of a suitably rigid insulating material. In operation, the injection needle 120 supplies injection substance to a target tissue area and the micropatch member 100 operates in conjunction with a power supply to cause electroporation of the target tissue.

Figure 2:
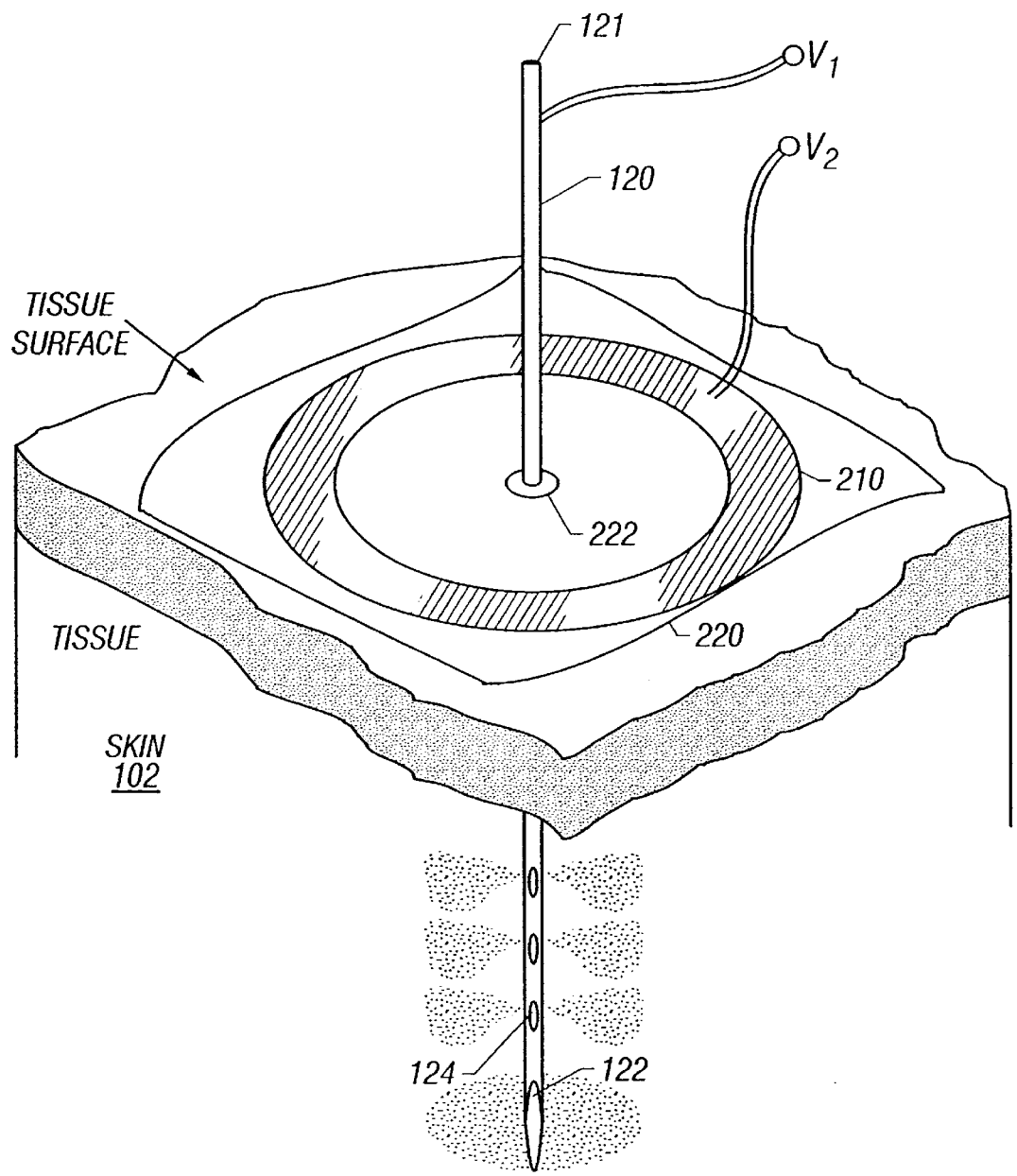
FIG. 2 shows an electroporation applicator that replaces the micropatch member 100 in FIG. 1 with a ring-shaped electrode 210.

FIG. 2 shows an electroporation applicator wherein the micropatch member 100 depicted in FIG. 1 is replaced with a ring-shaped electrode 210, providing voltage V2. Unlike the applicator shown in FIG. 1, the injection needle 120 in this embodiment also functions as an electrode, providing voltage V1. Hence, at least a part of the injection needle 120 must be formed of an electrical conductor. In the embodiment illustrated in FIG. 2, the needle 120 is formed of a metal. The ring-shaped electrode 210 may be in any shape, including but not limited to, a circular ring as shown, a square ring, or the like. An electrical insulating shield 220 is implemented to provide a support to the ring-shaped electrode 210 and to electrically insulate a tissue under treatment from the electrode 210. A through hole 223 is formed on shield 220 within the center opening of the ring-shaped electrode 210 for positioning the injection needle 120. The needle electrode may be modified to provide for radial delivery of an injection substance, for example, by providing one or more holes disposed along its length and proximal to the needle tip, wherein said holes are in fluid communication with the hollow interior of the injection needle.

An electrical control circuit (not shown) is connected to both the injection needle 120 and the ring-shaped electrode 210 to produce desired electrical pulses, causing electroporation and augmented delivery of the injection substance to the target tissue.

Figure 3:
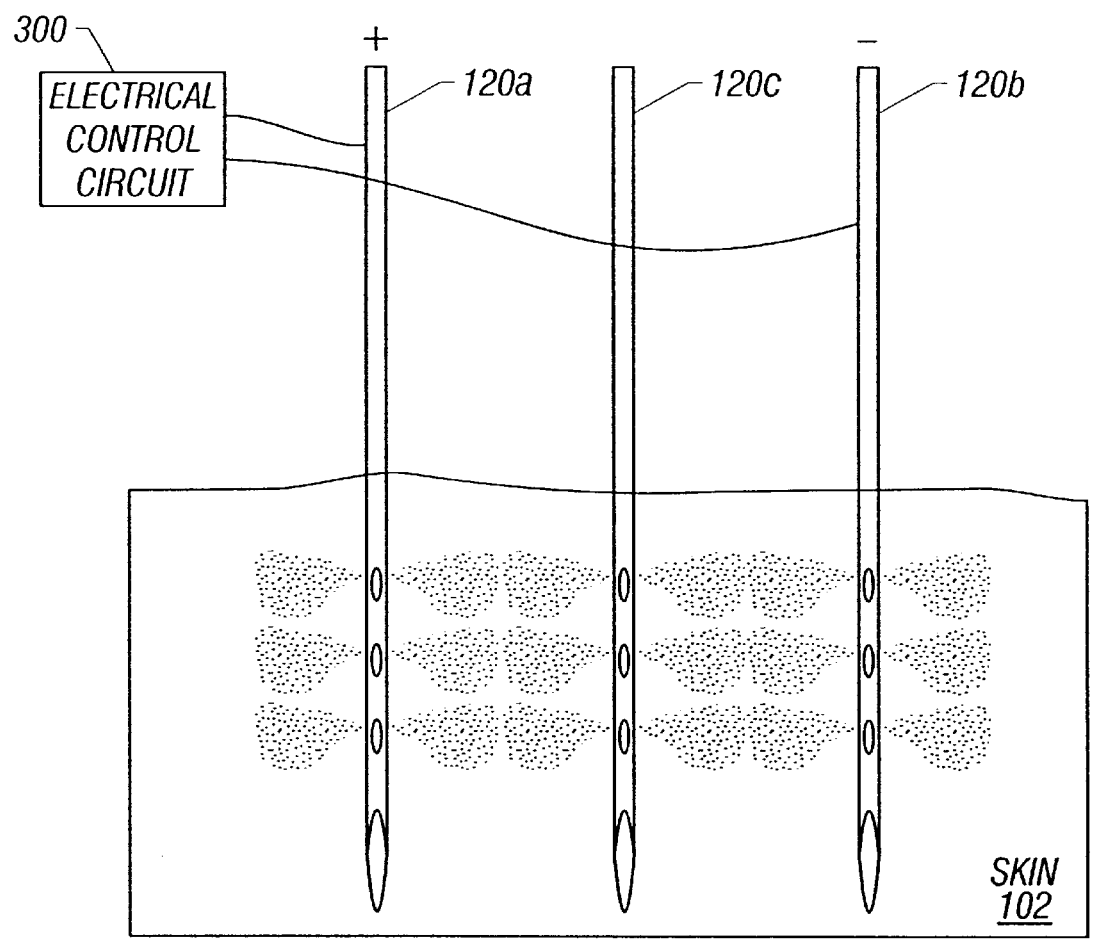
FIG. 3 shows a device having three injection needles 120A, 120B, and 120C connected to an electrical control circuit 300 to function as a pair of electrodes.

FIG. 3 shows a device having a plurality of paired electrode needles and at least one injection needle. In the embodiment depicted in FIG. 3, the electrode has three needles 120A, 120B, and 120C. Needles 120A and 120B are connected to an electrical control circuit 300 to function as a pair of electrodes. Additional paired electrode needles may be employed. The needle 120C is not used to apply electrical pulses to the tissue under treatment but is used as an injection port to supply injection substance to the electroporated tissue area. Substantially contemporaneously with the injection of an injection substance, voltage difference is applied between the needle electrodes 120 to produce desired electrical pulses, causing electroporation and augmented delivery of the injection substance to the target tissue. The injection needle may be modified to provide for radial delivery of an injection substance, for example, by providing one or more holes disposed along its length and proximal to the needle tip, wherein said holes are in fluid communication with the hollow interior of the injection needle.

FIG. 4A shows an electroporation device based on the device shown in FIG. 2. A suction generating device such as a syringe 410 is implemented to hold an injection needle electrode 420 and a ring electrode 430. In the depicted embodiment, the suction device is a syringe 410 having a piston 412 which is slidably with, and sealingly disposed about the injection needle electrode 420. As used herein, "sealingly disposed about" means that the piston is fitted around the needle closely enough that a partial vacuum can be created upon withdrawal of the piston. The close fit may be facilitated, for example, by providing a gasket, or the like. In this manner, when the piston 412 is retracted, or suction is otherwise generated, a partial vacuum is created in the syringe 410 and skin to which the device is applied is partially lifted up by action of the vacuum (FIG. 4B). This facilitates the penetration of the skin by the injection needle electrode 420. Substantially contemporaneously with the injection of an injection substance, voltage difference is applied between the needle electrode 420 and the ring electrode 430 so that electrical pulses can be generated, causing electroporation and augmented delivery of the injection substance to the target tissue.

Figure 5A:
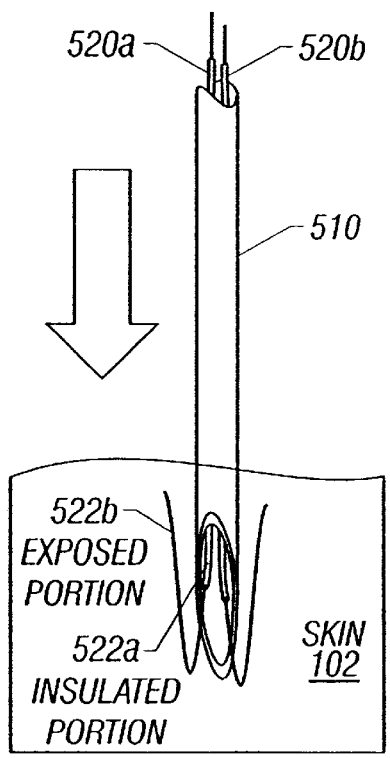
FIGS. 5A and 5B show a needle applicator having a hollow needle 510 and two electrical wires 520A and 520B that are held in the hollow portion of the needle 510.
Figure 5B:
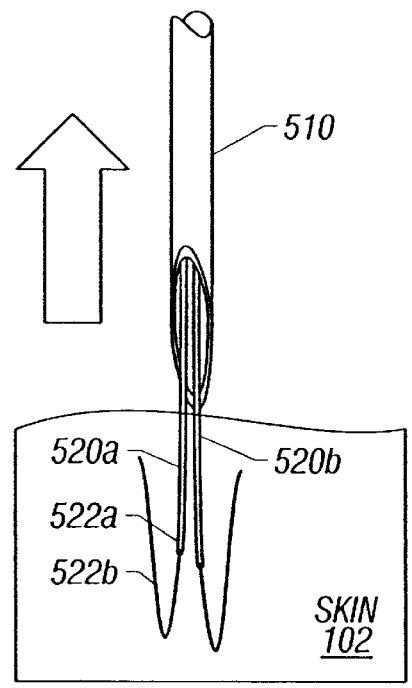

FIGS. 5A and 5B show a needle applicator having a hollow needle 510 and two electrical wires 520A and 520B that are held in the hollow portion of the needle 510. Each wire (e.g., 520A) has an insulated portion (e.g., 522A) and an exposed tip portion (e.g., 522B). In operation, the needle 510 penetrates a tissue and then is withdrawn to "plant" the exposed tip portions of the two wires 520A and 520B in the tissue (FIG. 5B). Substantially contemporaneously with the injection of an injection substance, voltage difference is applied between the wires 520A and 520B such that electrical pulses can be generated, causing electroporation and augmented delivery of the injection substance to the target tissue.

FIG. 6 shows a pair of needle electrodes 610 and 620 that have substance-releasing sections 612 and 622 near the needle tips. The substance-releasing sections 612 and 622 are configured to have an injection substance (e.g., a selected DNA) associated therewith. The substance-releasing sections may be formed of any biocompatible suitably absorbent material or material to which injection substance will adhere. Materials contemplated for use as substance-releasing sections include lipids, cationic lipids, heparin, hyaluronic acid, and the like. When the needles are penetrated within a tissue, electrical pulses are applied to the needle electrodes 610 and 620 so that injection substance applied substantially contemporaneously therewith can be electroporated into the cells between the electrodes.

As used herein, "biocompatible" or "biocompatible material" means a material that is suitable for introduction into the human body for therapeutic purposes.

FIG. 7 shows a single needle applicator. A needle 710 has a hollow center portion and at least four holes 712A, 712B, 714A, and 714B on the side walls proximal to the needle tip. Paired holes (e.g., 712A and 712B) are preferably arranged relatively proximal and distal to the needle tip along the same side of the needle body. Holes 714A and 714B are similarly arranged along the needle body but are radially spaced from holes 712A and 712B. The needle 710 is either formed of an insulator or coated with an insulating layer. Two electrical wires 720 and 730 located in the hollow center portion of the needle respectively run through the holes 714A, 714B and 712A, 712B to so that wire sections 720A and 720B are exposed on the exterior of the needle body 710. Each wire is coated with an insulator layer except for the exposed section. Different electrical potentials are applied to the wires 720 and 730 to produce electrical pulses between the exposed sections 720A and 720B. Additional holes may be formed near the holes 712A, 712B, 714A, 714B for delivering an injection substance.

Figure 8:
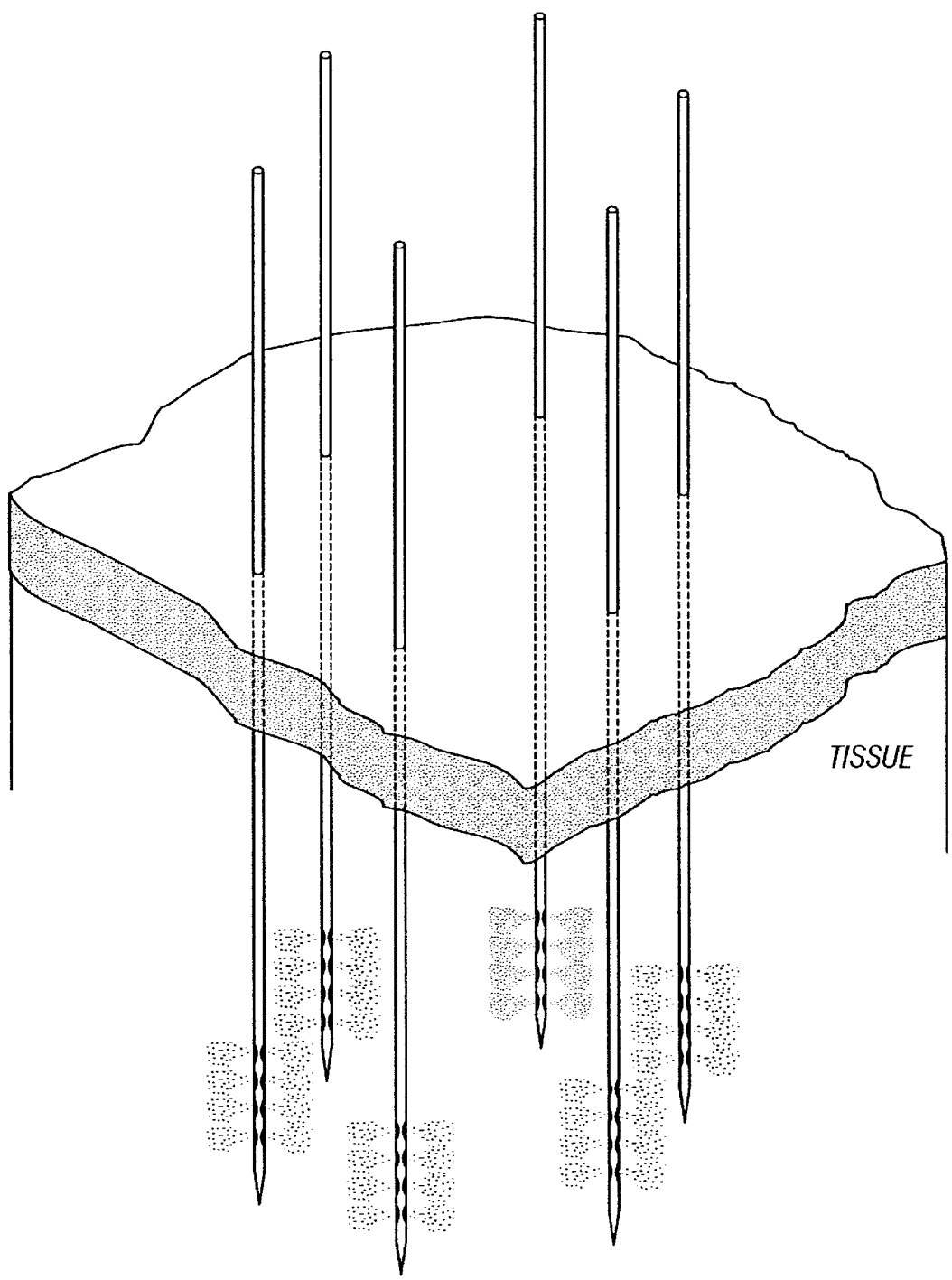
FIG. 8 shows an applicator having an array of 6 needle electrodes. Each needle electrode is used to apply both electrical pulses and a therapeutic agent.

FIG. 8 shows an applicator having an array of 6 needle electrodes. Each needle electrode is used to apply both electrical pulses and an injection substance. As illustrated, holes are formed on the side walls near the needle tip for releasing an injection substance into the tissue.

Figure 9:
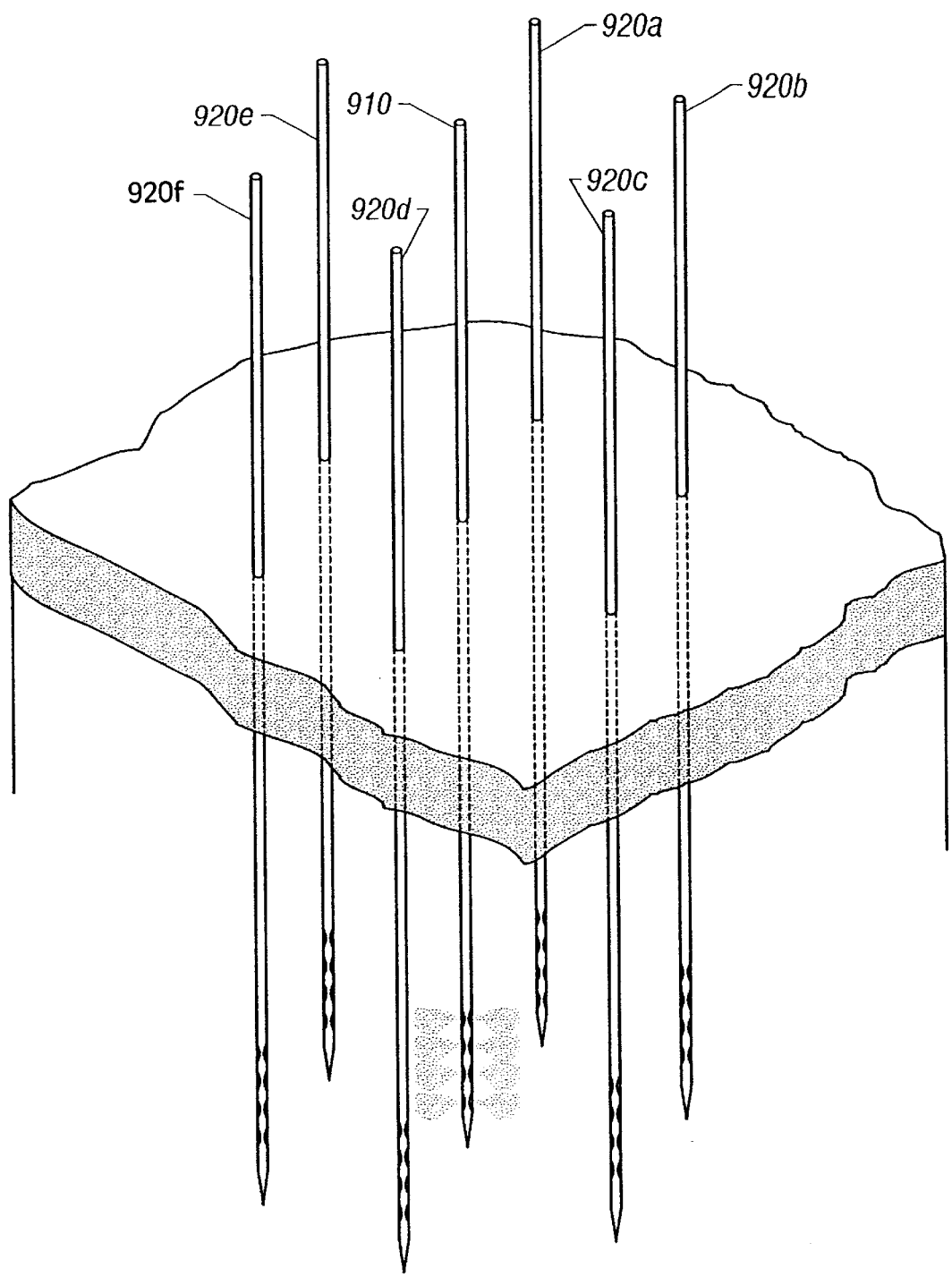
FIG. 9 shows another applicator having an array of needle electrodes (920A, 920B, etc.). A substance-releasing needle 910 is located in the center of the array and has holes near the needle tip for releasing a DNA.

FIG. 9 shows another applicator having an array of needle electrodes (920A, 920B, etc.). A substance-releasing needle 910 is located in the center of the array and has holes near the needle tip for releasing an injection substance. Substantially contemporaneously with the injection of an injection substance, voltage difference is applied between pairs of needles such that electrical pulses can be generated, causing electroporation and augmented delivery of the injection substance to the target tissue.

The needle 910 may be either electrically active to be pulsed against the surrounding needle electrodes or is electrically passive.

As used herein, "injection substance" means any therapeutic agent to be delivered to the target tissue. As described herein, therapeutic agents contemplated for use in the practice of the present invention include nucleic acids, polypeptides, chemotherapeutic agents and the like.

In accordance with another embodiment of the present invention, there are provided electrode kits for use in conjunction with electroporation therapy, each kit containing the components of the electrodes described herein. For example, in one aspect, there is provided an electrode kit comprising a micropatch electrode, and an injection needle, optionally comprising one or more holes disposed along its length and proximal to the needle tip, wherein the holes are in fluid communication with the hollow interior of the injection needle.

With all of the above electroporation devices, a brief time of iontophoresis may be applied to distribute the DNA between the electrodes before pulsing for electroporation. The needles can be used for iontophoresis between two or among three or more needles. Iontophoresis can also be performed between any needle and other electrodes such as between the injection needle 120 and the ring electrode 210 in FIG. 2. Therefore, in accordance with another embodiment of the present invention, there are provided methods for introducing therapeutic agents into skin cells of a subject, said method comprising employing an electroporation method as described herein in conjunction with iontophoresis and or electroincorporation.

Additional functional components that can be added to the invention electrical apparatus include, for example, an iontophoresis unit (IPH), which can be used in combination with an electrical impulse to transdermally introduce a greater amount of the composition into and/or across the skin than pulsing alone, or that can drive the composition deeper into the skin and/or muscle, if desired. A controlling means (e.g., a switching unit), such as an automated switch, optionally programmable, may be used to control any of the parameters of invention apparatus, including, for example, application of pulse alone, the time between applying the impulse and applying IPH, as well as optionally controlling the time during which IPH is applied. Each parameter will be determined by the composition introduced, the desired effect, the concentration etc. In one aspect of this embodiment, electrodes can be operated by an electroporation unit and an IPH unit respectively in a sequential manner. More specifically, two caliper electrodes can be disposed on either side of a skin fold (e.g., electrodes 1 and 2 on the left side and electrodes 3 and 4 on the right side). In electroporation mode electrode 1 is pulsed against electrode 2, likewise electrode 3 is pulsed against electrode 4. In IPH mode, electrode 1 is connected to electrode 2 (with either positive or negative polarity) while electrode 3 is connected to electrode 4 with an opposite polarity; then electrodes 1 and 2 will be pulsed against electrodes 3 and 4. Of course, these operation parameters can be set or programmed into the mini-generator.

A vibration unit also can optionally be included in the apparatus, which can be used in combination with an electrical impulse to transdernally introduce a composition into and/or across the skin, if desired. A phonophoresis unit, which can transdermally introduce a composition into the skin by means of ultrasound, also can optionally be included in the apparatus, if desired. Thus, by applying vibration or ultrasound before, after or during pulsing and/or iontophoresis, the composition can be driven deeper into the target tissue or a greater amount of the composition can be driven into the target tissue than pulsing alone. As above, a switching unit, such as an automated switch, optionally programmable, could be used to control the time between applying the impulse and applying vibration or ultrasound, as well as optionally controlling the time during which impulse, vibration or ultrasound is applied.

A means for administering a composition can optionally be included in the electrical apparatus, which can be used to administer the composition to the target tissue prior to, substantially contemporaneously with, or after applying an electric pulse, iontophoresis, vibration or ultrasound, in their various embodiments. Depending on the specific formulation, a composition can be incorporated into a patch reservoir (e.g., as a nicotine patch), which is then attached both to the electrode and the skin. Formulations employed for IPH are advantageously used in this manner.

As used in the above context, the term "substantially contemporaneously" means that the electric pulse and the composition are applied to the skin reasonably close together in time. Preferably, the composition is administered prior to or concurrently with electropulsing. When applying multiple electrical impulses, the composition can be administered before or after each of the pulses, or at any time between the electrical pulses. When applying any auxiliary electrically-based therapy (i.e., IPH, EI, and the like), vibration or ultrasound, the composition can be administered before or after each, and at any time between.

Although electrodes of the present invention are designed to work with commercially available electroporation power supplies, the invention apparatus can have a variety of other functionalities in addition to the optional controlling means for applying an electric pulse, indicating means and fastening means. For example, the apparatus can have an indicating means for indicating apparatus ready, the various pulse parameter settings (e.g., voltage, capacitance, pulse duration, time delay between pulses, pulse wave type), pulse(s) applied, parameters of the applied pulse(s) (e.g., voltage, capacitance, pulse duration, pulse wave type, number of pulses) or a combination thereof. Such indicating means can be visual, audible, or a combination thereof. For example, a single audible "beep" can indicate that the "apparatus is ready," two audible "beeps" can indicate that a pulse has been correctly applied and three audible "beeps" can indicate a malfunction or that the pulse was not or was improperly applied. Visual indicating means include analog or digital alpha-numeric displays (e.g., LCD, LED and the like), as in watches, and further can include illuminating means for low light visualization, for example, by white light, electroluminescent backlighting for LCD or electroluminescent lamps (i.e., INDIGLO™), or by various fluorescent or radioactive illuminating compositions, and the like.

Additional "user friendly" functions include the aforementioned controlling means for applying an electric pulse (e.g., pushbutton, knob, lever switch, dial and the like) as well as means for adjusting parameters (e.g., pushbutton, knob, lever switch, dial and the like) including, for example, pulse duration, voltage, capacitance, field strength, number, wave type, and the like. Means for adjusting, setting, storing or retrieving one or more pulse parameters also are included herein. Such means include traditional mechanical electronic controls (e.g., a selector switch controlling each parameter in which the switch has a plurality of settings; exemplary pulse length settings, 5 msec, 10 msec, 25 msec, 35 msec, 50 msec, for example) as well as a chip control (e.g., silicon wafer types commonly used in the computer industry) which is controlled, for example, by a pushbutton interface, as in watches for example. A chip, optionally removable from the apparatus or, user and/or manufacturer programmable for control of the various pulse parameters set forth herein also is contemplated. Storage capacity of such a chip is sufficient to provide virtually unlimited fine control of the various parameters, as well as storing different pulse parameter settings for different compositions, users and the like. As each of the various electronic functionalities of the invention apparatus described herein can be controlled or managed by a computer chip, a chip affords the option of additionally incorporating software, if desired, said software optionally user programmable.

In addition to efficacy, both sensation and user safety are important. Thus, in another embodiment, the invention further provides an apparatus having means for preventing applying excess pulse voltage, duration, field strength and/or number. Any means which passively or actively interrupts or disrupts the electric circuit, including fuses, circuit breaker switches, and the like, or devices that actively monitor the various pulse parameters and interrupt or disrupt the electric circuit to prevent excess pulse voltage, duration, field strength, pulse number from being applied can be incorporated into the circuit path. Those skilled in the art of electrical devices will know of other protective elements that prevent applying excess pulse voltage, duration, field strength or number.

The electric pulse can be provided by any electronic device that provides an appropriate electric pulse or electric source sufficient for transdermally introducing a composition into skin and/or muscle. The nature of the electric field to be generated is determined by the nature of the tissue, the size of the selected tissue and its location. It is desirable that the field be as homogenous as possible and of the correct amplitude. Excessive field strength results in lysing of cells, whereas a low field strength results in reduced efficacy. The electrodes may be mounted and manipulated in many ways including but not limited to those in the parent application. The electrodes may be conveniently manipulated on and by forceps to internal position.

The waveform of the electrical signal provided by the pulse generator can be an exponentially decaying pulse, a square pulse, a unipolar oscillating pulse train, a bipolar oscillating pulse train, or a combination of any of these forms. The nominal electric field strength can be from about 10 V/cm to about 20 kV/cm (the nominal electric field strength is determined by computing the voltage between electrode needles divided by the distance between the needles). The pulse length can be about 10 µs to about 100 ms. There can be any desired number of pulses, typically one to 100 pulses per second. The wait between pulses sets can be any desired time, such as one second. The waveform, electric field strength and pulse duration may also depend upon the type of cells and the type of molecules that are to enter the cells via electroporation. Each pulse wave form has particular advantages; square wave form pulses provide increased efficiencies in transporting compounds into the cells in comparison to exponential decay wave form pulses, and the ease of optimization over a broad range of voltages, for example (Saunders, "Guide to Electroporation and Electrofusion," 1991, pp. 227–47). Preferably, the waveform used is an exponential or a square wave pulse.

The electric fields needed for in vivo cell electroporation are generally similar in magnitude to the fields required for cells in vitro. Presently preferred magnitudes are in the range of from 10 V/cm to about 1300 V/cm. The higher end of this range, over about 600 V/cm, has been verified by in vivo experiments of others reported in scientific publications.

The nominal electric field can be designated either "high" or "low". It is presently preferred that, when high fields are used, the nominal electric field is from about 700 V/cm to 1300 V/cm and more preferably from about 1000 V/cm to 1300 V/cm. It is presently preferred that, when low fields are used, the nominal electric field is from about 10 V/cm to 100 V/cm, and more preferably from about 25 V/cm to 75 V/cm. In a particular embodiment of the present invention, it is presently preferred that when the electric field is low, the pulse length is long. For example, when the nominal electric field. is about 25–75 V/cm, it is preferred that the pulse length is about 10 msec.

It is presently preferred that practice of the therapeutic method of the invention utilizes the apparatus of the invention which provides an electrode apparatus for the application of electroporation to a portion of the body of a patient and comprises a support member, a plurality of needle electrodes mounted on said support member for insertion into tissue at selected positions and distances from one another, and means including a signal generator responsive to said distance signal for applying an electric signal to the electrodes proportionate to the distance between said electrodes for generating an electric field of a predetermined strength.

Alternatively, it is understood that other systems could be utilized in the therapeutic method of the invention (e.g., for low voltage, long pulse treatment), for example, a square wave pulse electroporation system. Exemplary pulse generators capable of generating a pulsed electric field include, for example, the ECM600, which can generate an exponential wave form, and the ElectroSquarePorator (T820), which can generate a square wave form, both of which are available from BTX, a division of Genetronics, Inc. (San Diego, Calif.). Square wave electroporation systems deliver controlled electric pulses that rise quickly to a set voltage, stay at that level for a set length of time (pulse length), and then quickly drop to zero. This type of system yields better transformation efficiency for the electroporation of plant protoplast and mammalian cell lines than an exponential decay system.

The ElectroSquarePorator (T820) is the first commercially available square wave electroporation system capable of generating up to 3000 Volts. The pulse length can be adjusted from 5 µsec to 99 msec. The square wave electroporation pulses have a gentler effect on the cells which results in higher cell viability.

The T820 ElectroSquarePorator is active in both the High Voltage Mode (HVM) (100–3000 Volts) and the Low Voltage Mode (LVM) (10–500 Volts). The pulse length for LVM is about 0.3 to 99 msec and for HVM, 5 to 99 µsec. The T820 has multiple pulsing capability from about 1 to 99 pulses.

Additional electroporation type apparatus are commercially available and can be used to generate the pulse for the invention apparatus and in practicing the invention methods.

The invention will now be described in greater detail by reference to the following, non-limiting examples.

EXAMPLES

Example 1

Electroporation of lacZ DNA

Figure 10A:
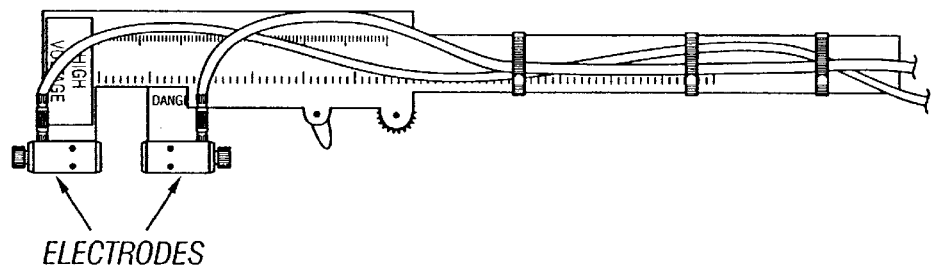
FIG. 10A depicts an example of a caliper type electrode (P/N 384, available from Genetronics, Inc.) comprising of two brass electrodes, each measuring about 1 cm×1 cm, mounted on a caliper scale which allows for accurate measurement of the inter-electrode distance.
Figure 10B:
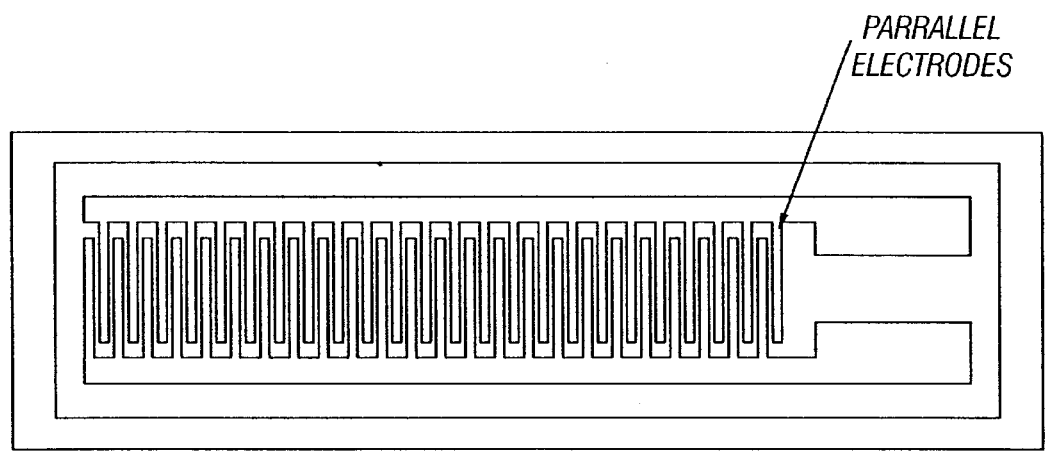
FIG. 10B depicts a meander electrode, comprising an array of interweaving electrode fingers. In this embodiment, the electrode finger width is about 2 mm and the electrode gap is about 0.2 mm.
Figure 11:
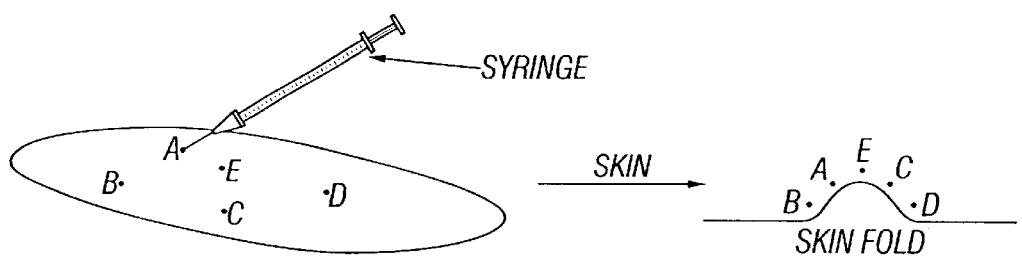
FIG. 11 depicts a method for introducing naked DNA into the skin comprising walk around intradermal injection of DNA into cites A–E, followed by electropulsing a thin fold of skin using a caliper electrode.
Figure 12:
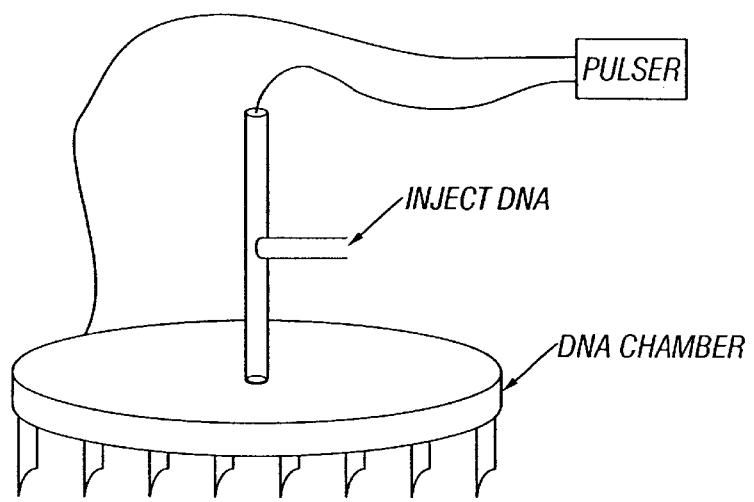
FIG. 12 depicts a microneedle electrode array with integrated container for therapeutic agent and therapeutic agent injector needle.

LacZ DNA (40 µg DNA in 20 µl Tris-EDTA), wherein the lacZ gene is under control of the CMV promoter, was topically applied to the skin of six to seven-week-old SKH1 hairless mice (female) (Charles River Laboratories. Wilmington, Mass.). A caliper electrode (FIG. 10A) was then placed on both sides of a skin-fold at the dorsal region of the mouse and electrical pulses were delivered. Unpulsed mice were used as pressure-only and blank controls. The skin was harvested for X-gal staining 3 days after application of the lacZ DNA.

Pulse application and electrical measurements: Three exponential decay pulses of amplitude 120 V and pulse length of 10 ms or 20 ms were administered from a BTX ECM 600 pulse Generator within about 1 minute. Pressure was maintained with the caliper for up to 10 min. following pulsing. A caliper-type electrode (1 cm$^2$ each electrode) was applied on a mouse skin-fold of about 1 mm in thickness. Resistance of the skin was measured before, during and after pulsing. Expression of lacZ DNA was assayed by X-gal staining with 0.1% nuclear fast red. Standard histological analysis was then carried out.

Figure 14A:
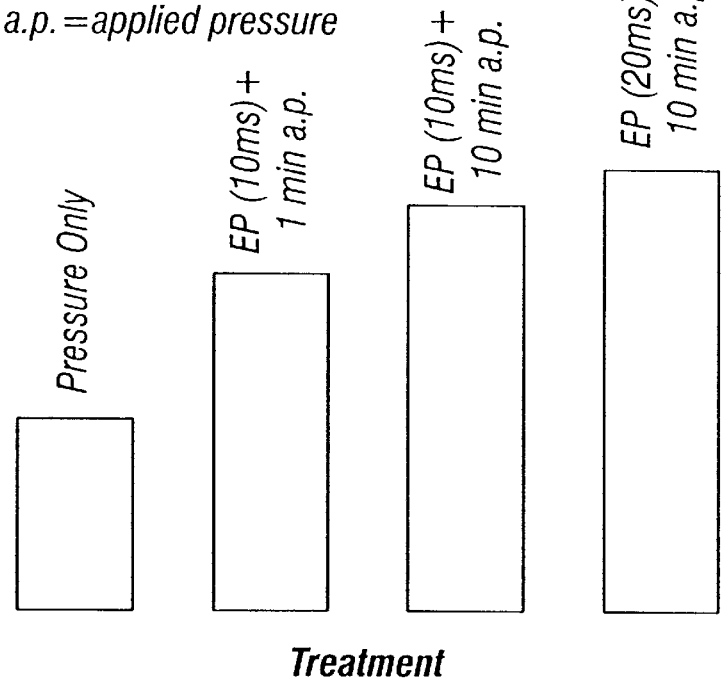
FIG. 14A graphically depicts the depth of lacZ gene expression under the experimental conditions described for FIG. 12 (A–D).
Figure 14B:
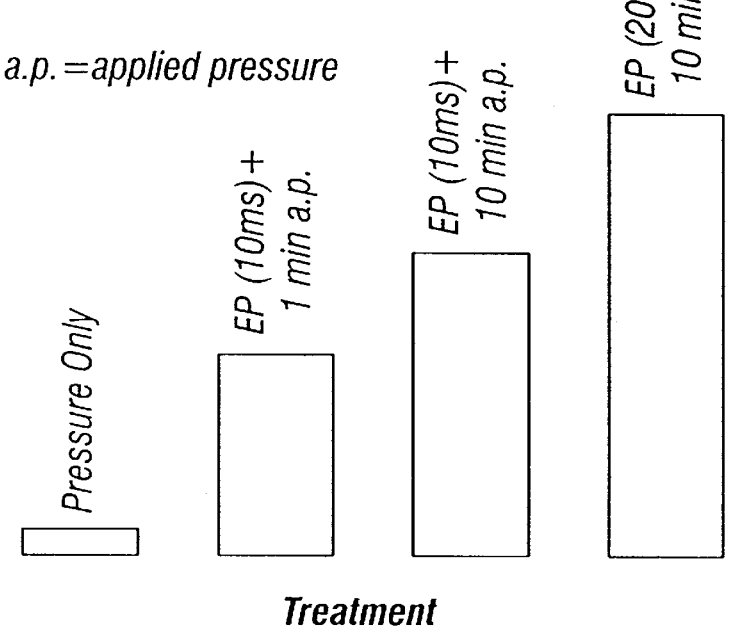
FIG. 14B graphically depicts the transfection efficiency of lacZ gene under the experimental conditions described for FIG. 13 (A–D).

Results: Typical results of gene expression after 3 days are shown in FIG. 13(a–d). A cell that expresses the lacZ gene undergoes blue staining of its cytoplasm when exposed to X-gal. Efficient gene transfer and expression were found in the dermis by pulsing and pressure treatment for 1 min. (FIG. 13b, FIGS. 14A and B). In the case of control (pressure only by caliper electrode), gene expression appeared only around hair follicles in the very upper layers of the skin with light blue staining (FIG. 13a, FIGS. 14A and B). This indicates that the electrical pulse creates new pathways to permit passage of DNA through the epidermis. Pressure maintained after the pulses, increases the depth as well as the efficiency of gene expression in the dermis. See, for example FIG. 13c, wherein a pulse of 10 ms delivered over about 1 min. was followed by caliper pressure being maintained for about 10 min. The third bar on graphs 14A and B show depth of penetration and efficiency of transfection, respectively, for the same parameters. A greater number of transfected cells and more intense lacZ gene expression were found with a 20 ms pulse length (FIG. 13d and FIGS. 14A and B, fourth bar, compared to 10 ms. The maximum depth of lacZ gene expression below the epidermis with pressure maintained for 10 minutes after pulsing was more than twofold that of the control in the hair follicles only.

The in vivo resistance measurements have demonstrated that the high resistance of the SC decreased dramatically during electroporation, and the recovery time (i.e., recovery of original resistance) depends on the electrical parameters. No β-gal activity was found in the control groups such as: no lacZ, pulse (i.e., electroporation); no pulse, lacZ; no lacZ or pulse. There was no evidence of tissue injury in the pulsed skin by visual observation as well as in histological studies.

Example 2
Electroporation of GFP

Figure 15:
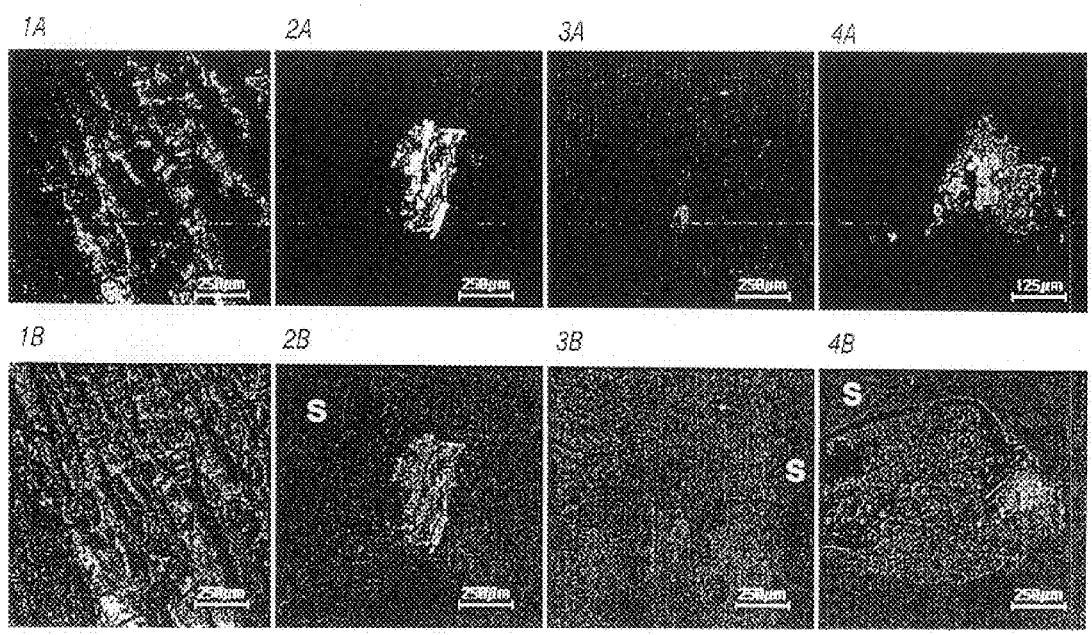
FIG. 15, panels 1 A/B–4 A/B show photomicrographs comparing integration and expression of GFP following application of plasmid DNA containing the GFP gene, followed by electroporation using meander or caliper type electrodes.

In vivo skin-targeted GFP gene delivery (FIG. 15): A procedure similar to that used in Example 1 was used for investigation the effectiveness of GFP expression in skin. Hairless mice were anesthetized with isoflurane inhalation and their dorsal hindquarter skin was swabbed with alcohol and air-dried. Fifty micrograms of a plasmid containing GFP and associated regulatory sequences (CMV promoter) was either applied topically or directly injected into the skin followed by electroporation with the caliper electrode or meander electrode. The animals were sacrificed three days later and skin of the treated area was excised and frozen. Frozen cross sections (12 μm) were immediately prepared. Viewing under a microscope with confocal fluorescent optics and FITC filtration, indicated GFP expression in the epidermal and dermal layers of the relatively thin murine skin (FIG. 15). The results of several different treatment regimens are depicted in FIG. 15. Panels 1A and 1B of FIG. 15 show photomicrographs of direct injection into abdominal muscle of plasmid. Panels 2 A/B and 3 A/B of FIG. 15 show the results of topical application of plasmid followed by three 100 V, 20 ms pulses applied using the BTX ECM 600 generator, using a caliper electrode (2 A/B) or a meander electrode (3 A/B). Panels 4 A/B of FIG. 15 show the results of subcutaneous injection of plasmid followed by three 120 V, 20 ms pulses applied using the BTX ECM 600 generator, using a caliper or meander electrode. Both the topical application and dermal injection of DNA gave detectable GFP expression with little apparent difference in the level of activity.

Example 3
In vitro Electroporation of Human Glioblastoma Cell Line SF-295

Figure 16A:
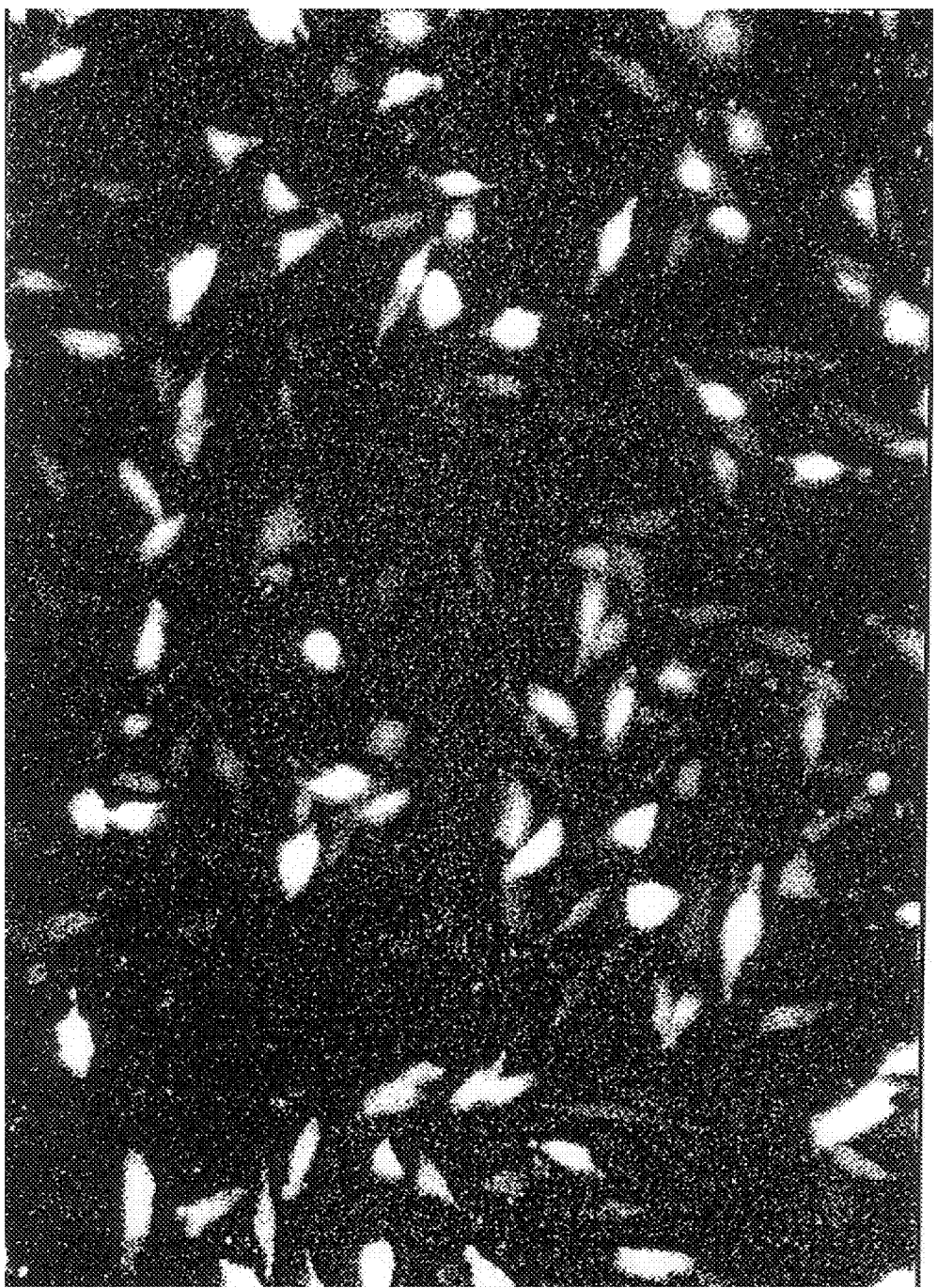
FIGS. 16A and 16B depict microphotomicrographs of SF-295 cells 24 hours post electroporation with unlabeled and labeled plasmid; each encoding GFP.
Figure 16B:

To evaluate and track the delivery of plasmid DNA to target cells, a fluorescently labeled vector using TOTO-1 (Molecular Probes, Inc.) was developed. The TOTO-1 molecule is attached to the green fluorescent protein (GFP)-expressing vector pEGFP-C1 (Clonetech). Both the plasmid, and the plasmid product (GFP) fluoresce under the same FITC excitation and filtration, and are thus both observable simultaneously under a microscope with confocal fluorescent optics and FITC filtration. (FIG. 16). 30 μg of unlabeled and 10 ug of TOTO-1 labeled plasmid was electroporated into the SF-295 cells and 24 hours later. GFP expression was assessed through an inverted fluorescent microscope. In FIG. 16A, (100× magnification, fluorescent light only) GFP expressing cells are visible as well as small green fluorescent dots that indicate TOTO-1 labeled plasmid within cells that are not expressing the plasmid. In FIG. 16B, (460× magnification) white light from a tungsten source was added to the fluorescent light to simultaneously illuminate the GFP positive and negative cells. This image shows the TOTO-1 labeled plasmid is aggregated into subcellular vesicles but the cells have not yet expressed GFP. Thus, the intracellular delivery and expression of a plasmid vector can be evaluated by this technique for in vivo skin applications.

Example 4
DNA Uptake in the Skin

DNA encoding the firefly luciferase gene was injected intradermally into skin of hairless mice (no shaving) or rats (after shaving of fur). DNA amounts shown in Table 1 were injected in 50 μl PBS as shallow as possible into the skin, using a 30 gauge needle. Electroporation was done with a caliper electrode (1 cm2) or with a Micro-patchII flat electrode. Where indicated, three 120V, 20 msec. pulses were given, using a BTX T820 instrument (BTX, Inc., San Diego, Calif.). The site of DNA injection was marked and the skin was removed 24 hours after treatment. Skin flaps were minced by scissor in lysis buffer provided in the commercial luciferase assay kit and luciferase activity was measured following the kit protocol. The results shown in Table 1 indicate that electroporation dramatically increase gene expression after intra-dermal DNA delivery into mouse and rat skin.

TABLE 1

EP Enhancement of
Lucerifase Activity after Intra-Dermal DNA Delivery (RLU)

|      | i.d. | i.d. + pulse |
|------|------|--------------|
|      | 20 μg in 50 μl | |
| Mice | 38   | 156,995 (caliper) |
|      | 7229 | 211,636 (caliper) |
|      | 1831 | 116,725 (micro-patchII) |
|      | 415  | 1,704,558 (micro-patchII) |
| Rat  | 57   | 194,398 (micro-patchII) |
|      | 5 μg in 50 μl | |
| Mice | 160  | 49,247 (caliper) |
|      | 9,021 | 57,134 (caliper) |
|      | 879  | 46,264 (micro-patchII) |
|      | 116  | 36,679 (micro-patchII) | background: <50, with or without pulse

Example 5
DNA Uptake in the Muscle

DNA encoding the firefly luciferase gene (20 μg in 50 μl PBS) was injected into the hind-limb muscle of hairless mice using a two needle electroporation array, where the injection needle also serves as negative electrode. The distance between the two electrodes was 2 mm. Where indicated, six pulses were given (20V per mm electrode distance, 50 msec., reversed polarity after 3 pulses; one pulse every 15 seconds) using the BTX T820 instrument. After 24 hours, the treated muscle was removed and minced by scissor for determination of luciferase activity using a commercial kit.

Genes encoding human growth hormone (hGH) or secreted alkaline phosphatase (SEAP) were injected into the hind-limb muscle of rats using the same device as used in mice and (where indicated) electroporation was done as described for mouse muscle. Growth hormone was measured in muscle tissue and serum using a commercial kit, SEAP activity was measured in serum using a commercial kit 24 hours after treatment. The results shown in Table 2 indicate that electroporation dramatically increases gene expression after intra-muscular DNA delivery in mice and rats.

TABLE 2

EP Enhancement of Gene Expression in Muscle

|  |  | i.m. | i.m. + pulse |
|---|---|---|---|
| hGH in rats (20 μg in 50 μl) (RLU) | | | |
|  |  | 3,341 | 41,465 |
|  |  | 3,462 | 27,540 |
| Serum |  | 1,027 | 1,449 |
| Background: | muscle: 3,242 | | |
|  | 3,397 | | |
|  | serum: 952 | | |
| Luciferase in mice (20 μg in 50 μl) (RLU) | | | |
|  |  | 576 | 27,441 |
|  |  | 140 | 74,637 |
| Background: 50,62 | | | |
| SEAP in rats (20 μg in 50 μl) (RLU in serum) | | | |
|  |  | 5,009 | 191,398 |
| Background: 2143 | | | |

Example 6
Immune Responses After Intramuscular DNA Delivery

An example of a model antigen is the Hepatitis B Virus surface Antigen (HBsAg). The gene encoding this antigen was cloned into an eukaryotic expression vector so that expression of the sAg gene is driven by the human elongation factor 1 promoter. Expression was verified by transient expression in B16 cells.

DNA was injected into the gracialis muscle of the hind limbs of Balb/c mice: 50 μg DNA in 50 μl PBS, both hind limbs were injected. One cohort of four animals was injected only (animals #1–4 in Table 3), one other cohort was treated with a two needle electrode array and pulsed: 20V per mm needle distance, 2×3 pulses at 50 msec. with polarity reversion after the first set of three pulses (animals #5–8 in Table 3). Two weeks after DNA delivery, 1 out of 4 mice was anti-HBSAG positive in the non EP treated cohort. All mice in the treated group were positive, pointing towards a positive effect of EP on the generation of an immune response. All mice were boosted four weeks post prime and tested again for antibody titers. The geometric mean titer (GMT) in the treated group was 193 mIU/ml, with ¾ mice having reached protective antibody levels. The GMT in the untreated group was 3.2 mIU/ml, with only ¼ mice reaching protective antibody titers. DNA immunization into the tibialis anterior muscle confirmed the above results: mice #1–4 in Table 4, untreated, GMT: 2.6 mIU/ml; mice #13-1 to 13-4, Table 3, EP treated, GMT: 13,547. In addition to showing the significant improvement of EP treatment on an immune response after DNA immunization, these data also show the superiority of the tibialis muscle for DNA immunization in mice.

Example 7
DNA Titration

To test whether electroporation could increase the efficiency of DNA vaccination after i.m. injection by allowing the use of lower DNA doses, DNA titration studies were performed. The need for extremely large doses of DNA is a major obstacle which has yet to be overcome in the DNA vaccination of larger animals than mice, and electroporation helps to overcome this problem. Except as otherwise noted, the experimental portions of this Example are as in Example 6.

Figure 17:
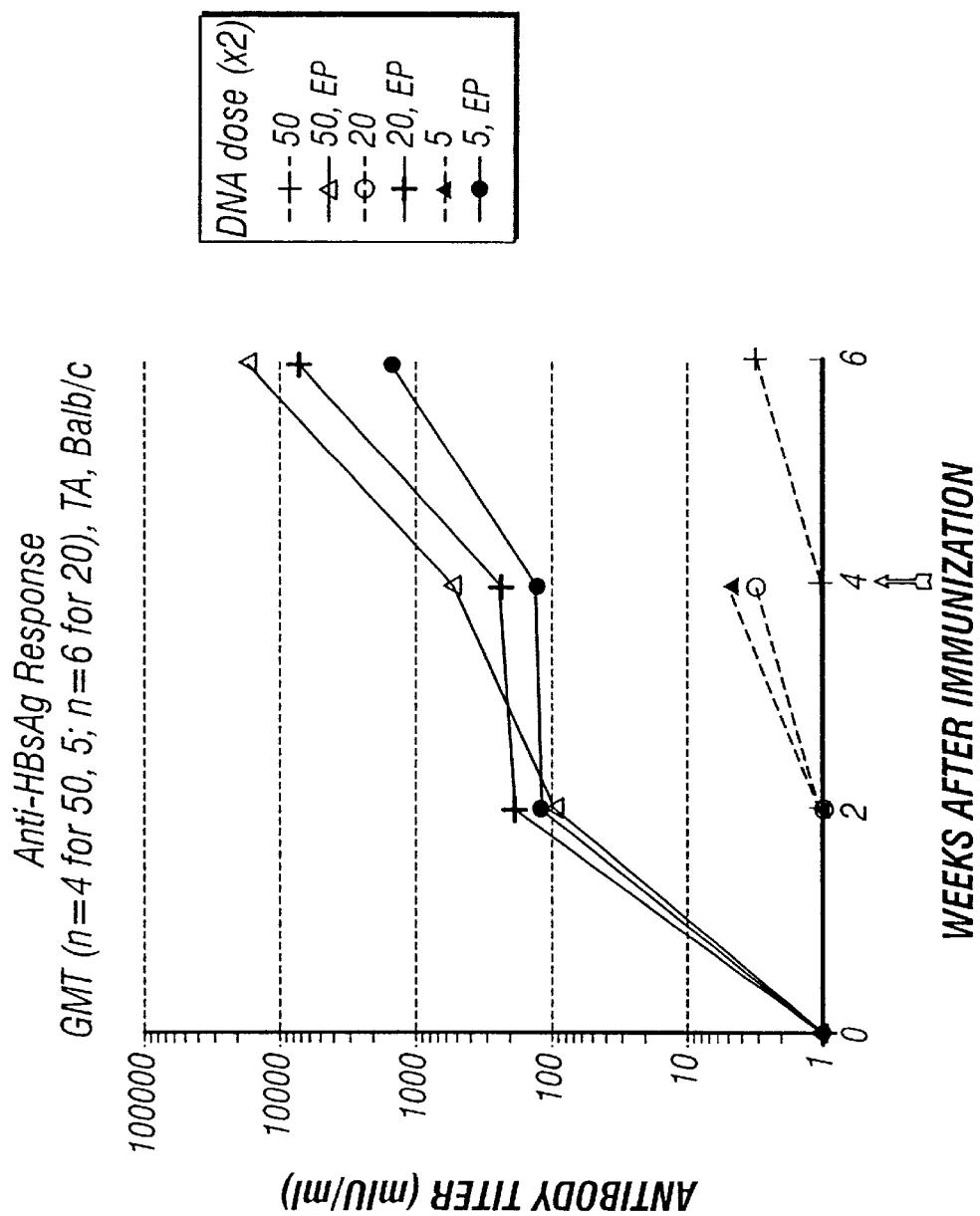
FIG. 17 graphically depicts the results of DNA immunization using 5 $\mu$g, 20 $\mu$g, and 50 $\mu$g in tibialis muscle of mice.

DNA immunizations with 5 μg, 20 μg, or 50 μg gave strong and consistent antibody responses two weeks after prime, which showed strongly boosted secondary responses after a booster immunization. These responses were achieved only with electroporation. (Mice #5–14, Table 4, #11, 12, Table 5, #13-1-13-4, Table 3). Down titration of the DNA used to immunize showed the consistent primary responses could be achieved with 3μ of DNA. With this amount, a booster immunization was necessary to give better then protective levels in all animals of this cohort. Mice #1–5, Table 6). One microgram or less DNA was found to be not sufficient to induce antibody responses, even after electroporation. (Mice #6–20, Table 6). Untreated cohorts receiving 20 μg or 5 μg of DNA showed GMTs of <10 mIU/ml (mice #1–10, Table 5). The results of DNA immunization using 5 μg, 20 μg, and 50 μg in tibialis muscle are summarized in FIG. 17.

TABLE 3

| cage 6–13 | | | | primary | | secondary |
|---|---|---|---|---|---|---|
| cage # | animal | μg DNA | pulse | 2 week | 4 week | 9 week |
| 6 | 1 | 50 | – | 300 | ± | 115 |
|  | 2 | 50 | – | 0 | 0 | 0 |
|  | 3 | 50 | – | 0 | 0 | 0 |
|  | 4 | 50 | – | 0 | 0 | 0 |
| 8 | 5 | 50 | + | 150 | 200 | 1680 |
|  | 6 | 50 | + | 40 | 0 | 0 |
|  | 7 | 50 | + | 140 | 120 | 581 |
|  | 8 | 50 | + | 280 | 560 | 1442 |
| 7 | 9 | 50 | ++ | 0 | 0 | 0 |
|  | 10 | 50 | ++ | 0 | 0 | 27 |
|  | 11 | 50 | ++ | 0 | 0 | 13 |
|  | 12 | 50 | ++ | 0 | 0 | 0 |
| 13 | 1 | 50 | + | 120 | 200 | 3868 |
|  | 2 | 50 | + | 310 | >>1000 | >>57000 |
|  | 3 | 50 | + | 40 | 240 | 17087 |
|  | 4 | 50 | + | 50 | 1000 | 8941 |

TABLE 4

| cage 14–17 | | | | primary | | secondary |
|---|---|---|---|---|---|---|
| cage # | animal | μg DNA | pulse | 2 week | 4 week | 9 week |
| 14 | 1 | 50 | – | 0 | 0 | 0 |
|  | 2 | 50 | – | 0 | 0 | 0 |
|  | 3 | 50 | – | 0 | ± | 0 |
|  | 4 | 50 | – | 0 | 0 | 50 |
| 15 | 5 | 50 | + | 200 | >>300 | 16000 |
|  | 6 | 20 | + | 105 | 80 | 2000 |
|  | 7 | 20 | + | 160 | >300 | 7800 |
|  | 8 | 20 | + | 160 | 320 | 2700 |
| 16 | 9 | 20 | + | 180 | 160 | 1800 |
|  | 10 | 20 | + | >300 | 300 | 23800 |
|  | 11 | 5 | + | 80 | 200 | 1500 |
|  | 12 | 5 | + | >300 | 140 | 1450 |
| 17 | 13 | 5 | + | 60 | 60 | 1100 |
|  | 14 | 5 | + | >300 | 120 | 900 |

TABLE 5

| cage 24–26 | | | | primary | |
|---|---|---|---|---|---|
| cage # | animal | μg DNA | pulse | 2 week | 7 week | secondary |
| 24 | 1 | 20 | – | 0 | 0 |  |
|  | 2 | 20 | – | ± | 0 |  |
|  | 3 | 20 | – | ± | 55 |  |
|  | 4 | 20 | – | 0 | 0 |  |
| 25 | 5 | 20 | – | 0 | 0 |  |
|  | 6 | 20 | – | 0 | 0 |  |
|  | 7 | 5 | – | 0 | 22 |  |

TABLE 5-continued

| | cage 24–26 | | | primary | | |
|---|---|---|---|---|---|---|
| cage # | animal | µg DNA | pulse | 2 week | 7 week | secondary |
| | 8 | 5 | − | 0 | 10 | |
| 26 | 9 | 5 | − | 0 | 0 | |
| | 10 | 5 | − | 0 | 0 | |
| | 11 | 5 | + | 160 | 315 | |
| | 12 | 5 | + | 170 | 154 | |

TABLE 6

| DNA titration | | | | primary | | secondary |
|---|---|---|---|---|---|---|
| Cage # | animal | µg DNA | pulse | 2 week | 4 week | 5 week |
| 27 | 1 | 3 | + | 300 | 120 | 336 |
| | 2 | 3 | + | 0 | 70 | 13.2 |
| | 3 | 3 | + | 0 | 0 | 51 |
| | 4 | 3 | + | 200 | 0 | 81.5 |
| 28 | 5 | 3 | + | 30 | 0 | 771 |
| | 6 | 1 | + | 0 | 0 | 0 |
| | 7 | 1 | + | 0 | 0 | 0 |
| | 8 | 1 | + | 0 | 0 | 0 |
| 29 | 9 | 1 | + | 0 | 0 | 0 |
| | 10 | 1 | + | 0 | 0 | 0 |
| | 11 | 0.5 | + | 0 | 0 | <10 |
| | 12 | 0.5 | + | 0 | 0 | <10 |
| 30 | 13 | 0.5 | + | 0 | 0 | 0 |
| | 14 | 0.5 | + | 0 | 0 | 0 |
| | 15 | 0.5 | + | 0 | 0 | <10 |
| | 16 | 0.1 | + | 0 | 0 | 0 |
| 31 | 17 | 0.1 | + | 0 | 0 | 0 |
| | 18 | 0.1 | + | 0 | 0 | 0 |
| | 19 | 0.1 | + | 0 | 0 | 0 |
| | 20 | 0.1 | + | 0 | 0 | 0 |

Figure 18:
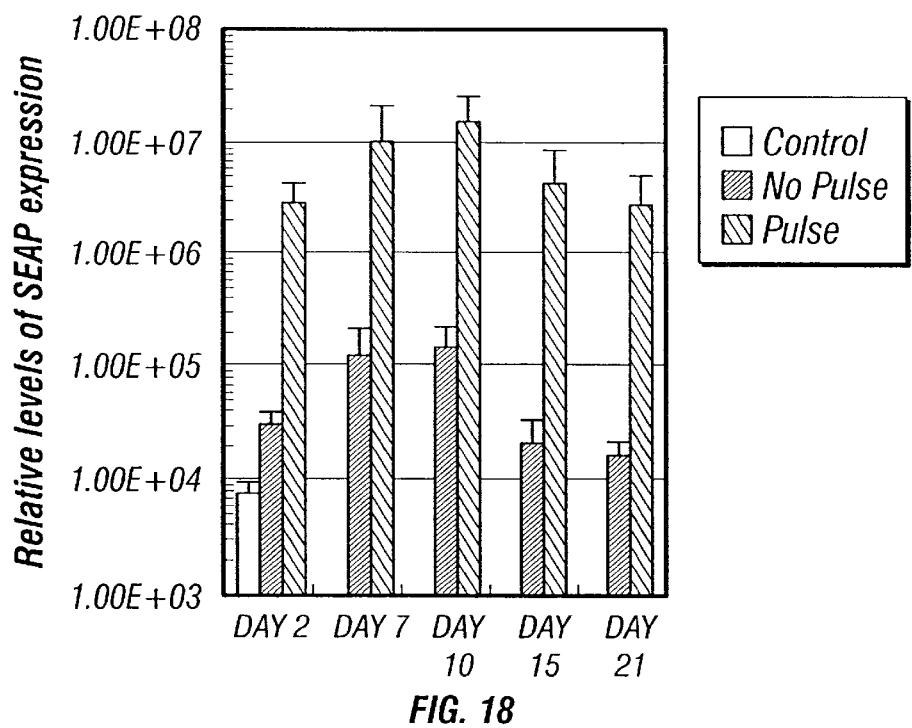
FIG. 18 depicts the dramatic increase in SEAP expression in blood obtained by combining electroporation with i.d. injection of plasmid encoding SEAP.

Example 8
Systemic Delivery of SEAP Plasmid DNA via Electroporation to Nude Mouse Skin In order to demonstrate that naked DNA can be transfected into skin cells with resulting expression and systemic delivery of gene product, fifty micrograms of SEAP DNA (plasmid DNA wherein SEAP is driven by CMV promoter) in IX PBS was injected i.d. into mouse flank followed by either electroporation or no electroporation. A square wave pulse at settings of 100V, 20 ms was applied using a meander electrode. Six pulses were applied with the polarity reversed after the first three pulses, and an interval of 100 ms between pulses. FIG. 18 shows that there is a dramatic increase in SEAP expression in blood that is greater than two logs. The length of expression is still high after 21 days in the nude mouse that is immune compromised.

Figure 19:
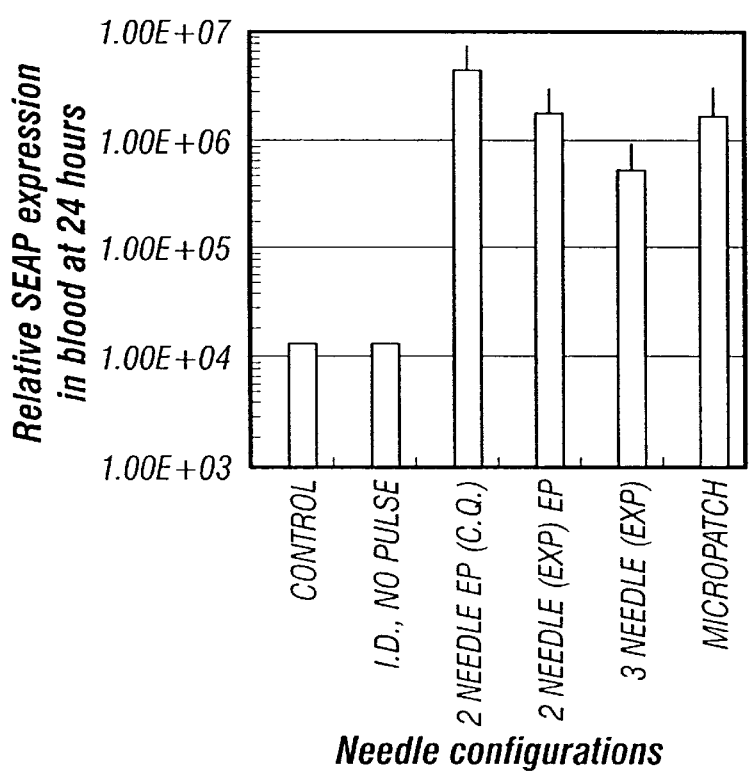
FIG. 19 graphically depicts the dramatic increases in SEAP expression in blood by using different configuration of shallow needle arrays when combining electroporation with i.d. injection of plasmid encoding SEAP.

Example 9
Shallow Needle Array and Micropatch Deliver SEAP Plasmid DNA to Nude Mouse Skin In order to test the effectiveness of different electrode types, electroporation experiments were conducted using the shallow needle array depicted in FIG. 20 and the micropatch array described in U.S. patent application Ser. No. 08/905, 240. Experimental conditions were as described in Example 8. FIG. 19 shows the dramatic increases in SEAP expression in blood by using different configurations of shallow needle arrays as well as the micropatch surface-type electrode. Square wave pulses were used with micropatch electrodes and 2-needle array (the higher bar in FIG. 19). The exponential pulses were used for 2- or 3-needle arrays (100 V, 20 ms, with polarity reversed after first three pulses). N=3 for micropatch and i.d. alone; n=2 for needle arrays; n=1 for control. Overall, electroporation again gave a two order of magnitude increase for SEAP expression. In the case of needle arrays (3 bars), only one needle injected DNA. However, DNA may be injected by more than one needle from the array.

Figure 21:
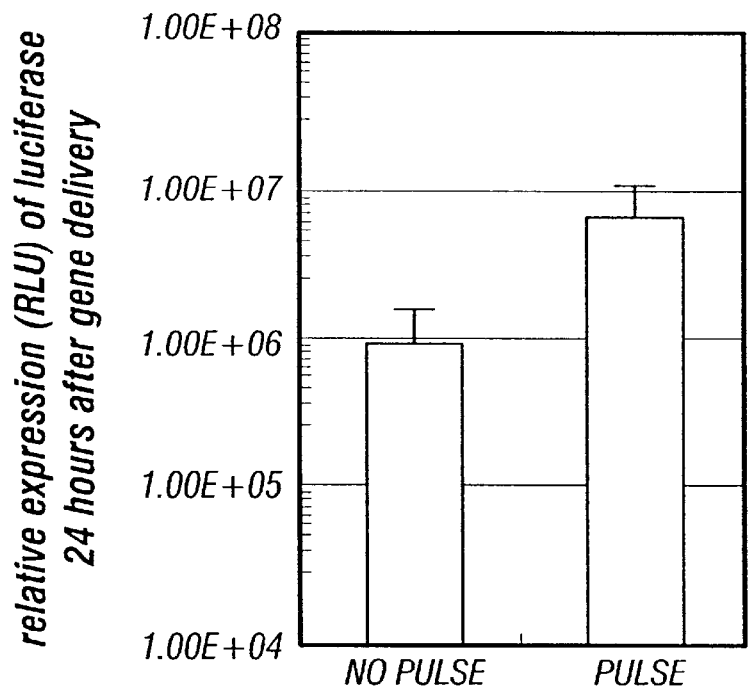
FIG. 21 shows the relative expression of luciferase (RLU) 24 hours after gene delivery to human skin xenografted onto nude mice, plus and minus electroporation.

Example 10
Use of Caliper Electrodes to Deliver CMV-luciferase Plasmid DNA to Human Skin Xenografted Nude Mice In order to demonstrate the capability if caliper electrode-based EPT to augment transfection of naked DNA into human skin (much thicker than murine skin), fifty micrograms of naked plasmid DNA containing the luciferase gene driven by the CMV promoter was i.d. injected into human skin xenografted onto nude mice. Luciferase expression was assayed 24 hours post DNA injection, plus and minus electroporation. Electroporation was as described in Example 8, employing a caliper electrode. The human skin grafts were excised from nude mice. The enzyme activity was measured by the spectrophotometer after homogenization and extraction. FIG. 21 shows the relative expression of luciferase (RLU) 24 hours after gene delivery. There was 7-fold increase for RLU in the pulsed group compared to i.d. injection alone.

Example 11
Comparison of Caliper vs. Meander Electrodes to Deliver CMV-luciferase Plasmid DNA to Hairless Mouse Skin In order to evaluate the relative effectiveness of caliper v. meander type electrodes, each was tested as follows.

Mice were anesthetized by isoflurane inhalation, weighed, numbered with permanent ink, and swabbed with alcohol at the site of electroporation. The skin area treated by caliper electrodes was about 2 $cm^2$.50 µg of naked plasmid DNA containing the reporter gene (luciferase driven by CMV promoter), at a concentration of 3.5 mg/ml in water, was administered onto the mouse skin. The DNA in solution, being slightly viscous, was moderately adsorbed by the skin and stayed in place. The electrode was then positioned at the site of DNA application, followed by electroporation, under the same electrporation conditions as described for Example 8. Luciferase gene expression was assayed at day 1 (24 hrs) after gene delivery.

Figure 22:
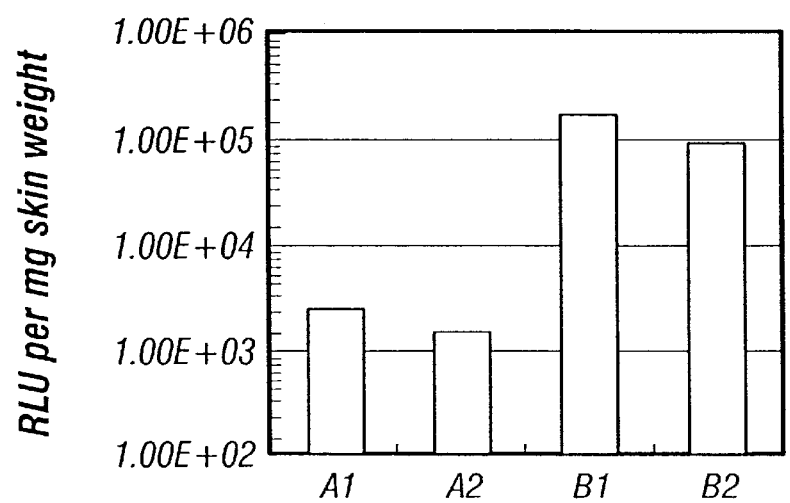
FIG. 22 depicts results obtained from the comparison of caliper vs. meander electrodes in delivering CMV-luciferase plasmid DNA to hairless mouse skin.

In order to investigate the location of gene expression in the skin layers, frozen sections of excised mouse skin were processed so that the full thickness skin (0.5 mm) was divided into two parts. The top part that was taken from outer most 150 um regions of the skin, the bottom part was the remainder of the skin. The enzyme activity was measured by the spectrophotometer after homogenization and extraction. The results were corrected for skin sample weight and the results are indicated graphically in FIG. 22. Bars A1 and A2 show meander electrode results, while bars B1 and B2 show caliper electrode results. A1 and B1 results were obtained from the outer 150 microns of skin, while A2 and B2 results were obtained from the remainder of the skin. Use of meander electrodes for electroporation resulted in much greater incorporation/expression of luciferase (i.e., two orders of magnitude). FIG. 22 further indicates that (1) a significant amount of luciferase DNA are delivered and expressed in the upper layers of the skin.

Example 12
Meander Electrodes Deliver CMV Beta-gal and Involucrin Beta-gal DNA in Nude Mice and Hairless Mice In order to test the relative expression achieved in mouse skin using genes driven by a CMV promoter as compared to the human involucrin promoter, the following experiment was conducted.

Fifty micrograms of plasmid DNA was administered to the skin via i.d. injection. Two sets of plasmids were used, containing the beta-galactosidase gene either driven by the CMV promoter or the human involucrin promoter. Pulsed (DNA(+) EP(+) and DNA(−) EP(+)) skin, and non-pulsed skin (DNA (+) EP (−)) was excised 24 hours after gene delivery. Electroporation was conducted as described in Example 8. Untreated skin (DNA (−) EP (−)) was also excised as a control. X-gal histochemical staining was used to illustrate the beta-galactosidase gene product.

Photomicrographs of skin cross sections were taken under the light microscope and intensive beta-galactosidase staining was observed with CMV beta-gal DNA delivery (i.d. injection+pulsing). It was distributed from epidermis to dermis. The expression of beta-gal DNA driven by the involucrin promoter was much weaker than with CMV promoter, and it was mostly located in the epidermal and upper dermal regions. No gene expression was observed with untreated skin, i.d. DNA injection alone, and pulsing without DNA.

These results demonstrate that it is feasible to target skin with a skin-specific promoter (i.e., involucrin). However, the involucrin promoter is much weaker than the CMV promoter.

Although the invention has been described with reference to the presently preferred embodiment, it should be understood that various modifications can be made without departing from the spirit of the invention. Accordingly, the invention is limited only by the following claims.

We claim:

1. A micropatch electrode for use with an electroporation apparatus, said micropatch electrode comprising a substantially planar array of patch elements, each patch element comprising two sets of electrodes, wherein each set of electrodes comprises a first electrode and a second electrode electrically insulated from one another, such that when different electric potentials are applied to said first and second electrodes, a voltage is produced therebetween; wherein the first electrode and second electrode and the distance therebetween are sized to create an electroporation-causing electric field in skin or muscle when a voltage of at least 10 V/cm is applied thereto.

2. A micropatch electrode according to claim 1, wherein said patch elements are separated by electrically insulating material.

3. A micropatch electrode according to claim 2, wherein said electrically insulating material can be pierced by an injection needle.

4. An electrode kit for use in conjunction with electroporation therapy, said kit comprising:
   a) a micropatch electrode according to claim 1, and
   b) an injection needle, optionally comprising one or more holes disposed along its length and proximal to the needle tip,
wherein said holes are in fluid communication with the hollow interior of said injection needle.

5. An electrode for use with an electroporation apparatus, said electrode comprising:
   a) a ring-shaped electrode having an electrically insulating shield with a centrally located through hole therein, wherein said electrically insulating shield provides support to said ring-shaped electrode and electrically insulates a tissue under treatment employing said electrode, and
   b) an electrically conducting injection needle for insertion through said through hole, said injection needle optionally comprising one or more injection holes disposed along its length and proximal to the needle tip, wherein said injection holes are in fluid communication with the hollow interior of said injection needle, and
wherein the electrode, the injection needle and distance therebetween is sized to generate an electroporation-causing electric field when a potential difference of at least 10 V per cm of the distance is applied between said ring-shaped electrode and said needle electrode.

6. An electrode for use with an electroporation apparatus, said electrode comprising a suction generating device comprising a ring electrode disposed about an injection needle electrode, such that when said ring electrode is contacted with skin of a subject and suction is generated by said suction generating device, said skin is pulled up around the injection needle electrode, causing the injection needle electrode to pierce the skin, and
wherein a potential difference applied to said ring-shaped electrode and said injection needle electrode creates a voltage therebetween.

7. An electrode according to claim 6, wherein said suction generating device further comprises a syringe comprising a piston slideably engaged with, and sealingly disposed about said injection needle electrode.

* * * * *